United States Patent
Lee et al.

(10) Patent No.: US 10,208,305 B2
(45) Date of Patent: Feb. 19, 2019

(54) RNA-YY1 INTERACTIONS

(75) Inventors: Jeannie T. Lee, Boston, MA (US); Yesu Jeon, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 830 days.

(21) Appl. No.: 14/130,769

(22) PCT Filed: Jul. 3, 2012

(86) PCT No.: PCT/US2012/045402
§ 371 (c)(1),
(2), (4) Date: Apr. 4, 2014

(87) PCT Pub. No.: WO2013/006619
PCT Pub. Date: Jan. 10, 2013

(65) Prior Publication Data
US 2014/0213460 A1    Jul. 31, 2014

Related U.S. Application Data

(60) Provisional application No. 61/504,660, filed on Jul. 5, 2011.

(51) Int. Cl.
| | |
|---|---|
| *C12N 1/10* | (2006.01) |
| *G01N 33/50* | (2006.01) |
| *C40B 30/00* | (2006.01) |
| *G01N 33/574* | (2006.01) |
| *C12N 15/10* | (2006.01) |
| *G01N 33/68* | (2006.01) |

(52) U.S. Cl.
CPC ..... *C12N 15/1048* (2013.01); *C12N 15/1072* (2013.01); *C12N 15/1093* (2013.01); *G01N 33/5011* (2013.01); *G01N 33/574* (2013.01); *G01N 33/57484* (2013.01); *G01N 33/6872* (2013.01); *G01N 2500/02* (2013.01)

(58) Field of Classification Search
CPC ................................ C12N 15/10; G01N 33/50
USPC .......................................................... 506/1
See application file for complete search history.

(56) References Cited

U.S. PATENT DOCUMENTS

| | | | |
|---|---|---|---|
| 2005/0037385 A1 | 2/2005 | Choo et al. | |
| 2008/0311039 A1* | 12/2008 | Bonavida | C07K 14/4702 424/9.1 |
| 2010/0267573 A1* | 10/2010 | Keene | C12Q 1/6804 506/9 |
| 2014/0142160 A1* | 5/2014 | Lee | C12N 15/113 514/44 A |
| 2014/0213460 A1* | 7/2014 | Lee | C12N 15/1048 506/1 |

FOREIGN PATENT DOCUMENTS

| | | |
|---|---|---|
| WO | 2004/099382 | 11/2004 |
| WO | WO 2004/099382 | 11/2004 |
| WO | 2008/024499 | 2/2008 |
| WO | WO 2008/024499 | 2/2008 |
| WO | WO 2010/093860 | 8/2010 |
| WO | WO 2012/065143 | 5/2012 |
| WO | WO 2012/087983 | 6/2012 |
| WO | WO 2013/006619 | 1/2013 |

OTHER PUBLICATIONS

Jeon et al., YY1 Tethers Xist RN to the Inative X Nucleation Center, 2011, Cell, 146, 119-133.*
Donohoe et al., Indentification of a Ctcf Cofactor, YY1, for the X Chromosome Binary Switch, Molecular Cell, 2007, 25, 43-56.*
Deng et al., Yin Yang 1—A Multifaceted Protein Beyond a Transcription Factor, Transcription, 2010, 1(2), 81-84.*
Sarma et al., Locked Nucleic Acids (LNA) Reveal Sequence Requirements and Kinetics of Xist RNA Localization to the X Chromosome, PNAS, 2010, 107(51), 22196-22201.*
International Search Report and Written Opinion dated Nov. 1, 2012 in international application No. PCT/US2012/045402, 7 pgs.
Sarma Kavitha et al., "Locked nucleic acids (LNAs) reveal sequence requirements and kinetics of Xist RNA localization to the X chromosome," PNAS 107(51): 22196-22201 (2010).
Kim Jeong Do et al., "Identification of clustered YY 1 binding sites in imprinting control regions," Genome Research 16(7): 901-911 (2006).
Atchison et al., "Transcription factor YY1 functions as a PcG protein in vivo," EMBO J., 22:1347-1358 (2003).
Brockdorff et al., "The product of the mouse Xist gene is a 15 kb inactive X-specific transcript containing no conserved ORF and located in the nucleus," Cell, 71:515-526 (1992).
Brown et al., "The human XIST gene: analysis of a 17 kb inactive X-specific RNA that contains conserved repeats and is highly localized within the nucleus," Cell, 71:527-542 (1992).
Carninci et al., "The transcriptional landscape of the mammalian genome," Science, 309:1559-1563 (2005).
Castellano et al., "The involvement of the transcription factor Yin Yang 1 in cancer development and progression," Cell Cycle, 8(9):1367-1372 (2009).
Donohue et al., "Identification of a Ctcf cofactor, Yy1, for the X chromosome binary switch," Mol Cell., 25:43-56 (2007).
Donohoe et al., "The pluripotency factor Oct4 interacts with Ctcf and also controls X-chromosome pairing and counting," Nature, 460:128-132 (2009).
Essien et al., "CTCF binding site classes exhibit distinct evolutionary, genomic, epigenomic and transcriptomic features," Genome Biol., 10:R131 (2009).
Flanagan et al., "Cloning of a negative transcription factor that binds to the upstream conserved region of Moloney murine leukemia virus," Mol Cell Biol., 12:38-44 (1992).

(Continued)

*Primary Examiner* — Amy M Bunker
(74) *Attorney, Agent, or Firm* — Fish & Richardson P.C.

(57) ABSTRACT

Methods relating to obtaining libraries of YY1-binding long non-coding RNAs, libraries obtained thereby, and methods of use thereof.

5 Claims, 14 Drawing Sheets
Specification includes a Sequence Listing.

(56) References Cited

OTHER PUBLICATIONS

Fujita et al., "The UCSC Genome Browser database: update 2011," Nucleic Acids Res., 39(Database issue):D876-D882 (2011) doi: 10.1093/nar/gkq963. Epub Oct. 18, 2010.
Hariharan et al., "Delta, a transcription factor that binds to downstream elements in several polymerase II promoters, is a functionally versatile zinc finger protein," Proc Natl Acad Sci U S A., 88:9799-9803 (1991).
Hendrich et al., "Evolutionary conservation of possible functional domains of the human and murine XIST genes," Hum Mol Genet., 2:663-672 (1993).
Hochedlinger et al., "Ectopic expression of Oct-4 blocks progenitor-cell differentiation and causes dysplasia in epithelial tissues," Cell, 121:465-477 (2005).
Jensen et al., "CLIP: crosslinking and immunoprecipitation of in vivo RNA targets of RNA-binding proteins," Methods Mol Biol., 488:85-98 (2008).
Jeon et al., "YY1 tethers Xist RNA to the inactive X nucleation center," Cell, Jul. 8, 2011;146(1):119-33. doi: 10.1016/j.cell.2011.06.026.
Johnston et al., "Developmentally regulated Xist promoter switch mediates initiation of X inactivation," Cell, 94:809-817 (1998).
Kapranov et al., "RNA maps reveal new RNA classes and a possible function for pervasive transcription," Science, 316:1484-1488 (2007).
Kent et al., "The human genome browser at UCSC," Genome Res., 12(6):996-1006 (2002).
Khalil et al., "Many human large intergenic noncoding RNAs associate with chromatin-modifying complexes and affect gene expression," Proc Natl Acad Sci U S A., 106(28):11667-72 (2009).
Kim et al., "Identification of clustered YY1 binding sites in imprinting control regions," Genome Res., 16(7):901-911 (2006).
Kim et al., "YY1 as a controlling factor for the Peg3 and Gnas imprinted domains," Genomics, 89:262-269 (2007).
Kim et al., "YY1's role in DNA methylation of Peg3 and Xist," Nucleic Acids Res., 37:5656-5664 (2009).
Kohlmaier et al., "A chromosomal memory triggered by Xist regulates histone methylation in X inactivation," PLoS Biol., 2:E171 (2004).
Ku et al., "Genomewide analysis of PRC1 and PRC2 occupancy identifies two classes of bivalent domains," PLoS Genet., 4:e1000242 (2008).
Kuzmichev et al., "Histone methyltransferase activity associated with a human multiprotein complex containing the Enhancer of Zeste protein," Genes Dev., 16:2893-2905 (2002).
Landeira et al., "Jarid2 is a PRC2 component in embryonic stem cells required for multi-lineage differentiation and recruitment of PRC1 and RNA Polymerase II to developmental regulators," Nat Cell Biol., 12:618-624 (2010).
Lee et al., "A 450 kb transgene displays properties of the mammalian X-inactivation center," Cell, 86:83-94 (1996).
Lee et al., "Genetic analysis of the mouse X inactivation center defines an 80-kb multifunction domain," Proc Natl Acad Sci U S A., 96:3836-3841 (1999).
Lee et al., "Targeted mutagenesis of Tsix leads to nonrandom X inactivation," Cell, 99:47-57 (1999).
Lee, "Lessons from X-chromosome inactivation: long ncRNA as guides and tethers to the epigenome," Genes Dev., 23:1831-1842 (2009).
Lee, "The X as model for RNA's niche in epigenomic regulation," Cold Spring Harb Perspect Biol., 2:a003749 (2010).
Lee et al., "Yin Yang 1 positively regulates BRCA1 and inhibits mammary cancer formation," Oncogene, 31:116-127 (2012). doi: 10.1038/onc.2011.217. Epub Jun. 13, 2011.
Lee, "Epigenetic regulation by long noncoding RNAs," Science, 338:1435-9 (2012).
Li et al., "Jarid2 and PRC2, partners in regulating gene expression," Genes Dev., 24:368-380 (2010).
Licatalosi et al., "HITS-CLIP yields genome-wide insights into brain alternative RNA processing," Nature, 456(7221):464-469 (2008).

Lobanenkov et al., "A novel sequence-specific DNA binding protein which interacts with three regularly spaced direct repeats of the CCCTC-motif in the 5'-flanking sequence of the chicken c-myc gene," Oncogene, 5:1743-1753 (1990).
Margueron et al., "The Polycomb complex PRC2 and its mark in life," Nature, Jan. 20, 2011;469(7330):343-9. doi: 10.1038/nature09784.
Mendenhall et al., "GC-rich sequence elements recruit PRC2 in mammalian ES cells," PLoS Genet., 6:e1001244 (2010).
Mercer et al., "Long non-coding RNAs: insights into functions," Nat Rev Genet., 10:155-159 (2009).
Nesterova et al., "Characterization of the genomic Xist locus in rodents reveals conservation of overall gene structure and tandem repeats but rapid evolution of unique sequence," Genome Res., 11:833-849 (2001).
Ogawa et al., "Intersection of the RNA interference and X-inactivation pathways," Science, 320:1336-1341 (2008).
Park et al., "Isolation of a candidate repressor/activator, NF-EL (YY-1, delta), that binds to the immunoglobulin kappa 3' enhancer and the immunoglobulin heavy-chain mu E1 site," Proc Natl Acad Sci U S A., 88:9804-9808 (1991).
Pillet et al., "Characterization of the promoter region of the mouse Xist gene," Proc Natl Acad Sci U S A., 92:12515-12519 (1995).
Plath et al., "Role of histone H3 lysine 27 methylation in X inactivation," Science, 300:131-135 (2003).
Pugacheva et al., "Familial cases of point mutations in the XIST promoter reveal a correlation between CTCF binding and pre-emptive choices of X chromosome inactivation," Hum Mol Genet., 14:953-965 (2005).
Ringrose et al., "Epigenetic regulation of cellular memory by the Polycomb and Trithorax group proteins," Annu Rev Genet., 38:413-443 (2004).
Sarma et al., "Locked nucleic acids (LNAs) reveal sequence requirements and kinetics of Xist RNA localization to the X chromosome," Proc Natl Acad Sci U S A., 107:22196-22201 (2010).
Schwartz et al., "Polycomb complexes and epigenetic states," Curr Opin Cell Biol., 20:266-273 (2008).
Seto et al., "YY1 is an initiator sequence-binding protein that directs and activates transcription in vitro," Nature, 354:241-245 (1991).
Shen et al., "EZH1 mediates methylation on histone H3 lysine 27 and complements EZH2 in maintaining stem cell identity and executing pluripotency," Mol Cell., 32(4):491-502 (2008).
Shi et al., "Transcriptional repression by YY1, a human GLI-Krüppel-related protein, and relief of repression by adenovirus E1A protein," Cell, 67:377-388 (1991).
Stavropoulos et al., "Identification of developmentally specific enhancers for Tsix in the regulation of X chromosome inactivation," Mol Cel Biol., 25:2757-2769 (2005).
Takahashi et al., "Analysis of promoter binding by the E2F and pRB families in vivo: distinct E2F proteins mediate activation and repression," Genes Dev., 14:804-816 (2000).
Ule et al., "CLIP: a method for identifying protein-RNA interaction sites in living cells," Methods, 37(4):376-386 (2005).
Ule et al., "CLIP identifies Nova-regulated RNA networks in the brain," Science, 302(5648):1212-1215 (2003).
Wang et al., "Multifunctional transcription factor YY1: a therapeutic target in human cancer?," Expert Opin Ther Targets, 10(2):253-266 (2006).
Wassenegger et al., "RNA-directed de novo methylation of genomic sequences in plants," Cell, 76:567-576 (1994).
Wilkinson et al., "Polycomb recruitment to DNA in vivo by the YY1 REPO domain," Proc Natl Acad Sci U S A., 103:19296-19301 (2006).
Woo et al., "A region of the human HOXD cluster that confers polycomb-group responsiveness," Cell, 140:99-110 (2010).
Wutz et al., "A shift from reversible to irreversible X inactivation is triggered during ES cell differentiation," Mol Cell., 5:695-705 (2000).
Xu et al., "Evidence that homologous X-chromosome pairing requires transcription and Ctcf protein," Nat Genet., 39:1390-1396 (2007).

(56) References Cited

OTHER PUBLICATIONS

Yeo et al., "An RNA code for the FOX2 splicing regulator revealed by mapping RNA-protein interactions in stem cells," Nat Struct Mol Biol., 16(2):130-137 (2009).

Zaravinos et al., "Yin yang 1 expression in human tumors," Cell Cycle, 9(3):512-522 (2010).

Zhang et al., "Perinucleolar targeting of the inactive X during S phase: evidence for a role in the maintenance of silencing," Cell, 129:693-706 (2007).

Zhang et al., "Mapping in vivo protein-RNA interactions at single-nucleotide resolution from HITS-CLIP data," Nat Biotechnol., 29:607-614 (2011).

Zhao et al., "Polycomb proteins targeted by a short repeat RNA to the mouse X chromosome," Science, 322:750-756 (2008).

Zhao et al., "Genome-wide identification of polycomb-associated RNAs by RIP-seq.," Cell, 40:939-953 (2010).

International Preliminary Report on Patentability for App. Ser. No. PCT/US2012/045402, dated Jan. 7, 2014, 6 pages.

International Search Report and Written Opinion for App. Ser. No. PCT/US2012/045402, dated Nov. 1, 2012, 7 pages.

Beletskii et al., "RNA interference mapping demonstrates functional domains in the noncoding RNA Xist," Proceedings of the National Academy of Sciences of the United States of America, 98(16):9215-9220 (Jul. 2001).

Chen et al., "Decoding the function of nuclear long non-coding RNAs," Current Opinion in Cell Biology, 22(3):357-364 (Mar. 2010).

Chow et al., "Inducible XIST-dependent X-chromosome inactivation in human somatic cells is reversible," Proceedings of the National Academy of Sciences of the United States of America, 104(24):10104-10109 (Jun. 2007).

Donohoe et al., "Identification of a Ctcf cofactor, Yy1, for the X chromosome binary switch," Molecular Cell, 25(1):43-56 (Jan. 2007).

Jeon et al., "YY1 Tethers Xist RNA to the Inactive X Nucleation Center," Cell, 146(1):119-133 (Jul. 2011).

Liu et al., "The Transcription factor YY1 binds to negative regulatory elements in the human cytomegalovirus major immediate early enhancer/promoter and mediates repression in nonpermissive cells," Nucelic Acids Research, 22(13):2453-2459 (Jul. 1994).

Supplementary European Search Report issued in EP12806953 dated Feb. 6, 2015 (10 pages).

Thorvaldsen et al., "A YY1 Bridge for X Inactivation," Cell, 146(1):11-13 (Jul. 2011).

Australian Office Action in Australian Application No. 2012279114, dated Sep. 6, 2016, 2 pages.

Canadian Office Action in Application No. 2,844,144, dated Jan. 22, 2018, 10 pages.

* cited by examiner

SEQUENCE LISTING

<160> NUMBER OF SEQ ID NOS: 48

<210> SEQ ID NO 1
<211> LENGTH: 24
<212> TYPE: DNA
<213> ORGANISM: Artificial Sequence
<220> FEATURE:
<223> OTHER INFORMATION: synthetically-generated primers

<400> SEQUENCE: 1
ttatgtggaa gttctacata aacg                                          24

<210> SEQ ID NO 2
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 2
accgcacatc cacgggaaac                                               20

<210> SEQ ID NO 3
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 3
cggttcttcc gtggtttctc                                               20

<210> SEQ ID NO 4
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 4
ggtaagtcca ccatacacac                                               20

<210> SEQ ID NO 5
<211> LENGTH: 22
<212> TYPE: DNA
<213> ORGANISM: Artificial Sequence
<220> FEATURE:
<223> OTHER INFORMATION: synthetically-generated primers

<400> SEQUENCE: 5
gctggttcgt ctatcttgtg gg                                            22

<210> SEQ ID NO 6
<211> LENGTH: 23
<212> TYPE: DNA
<213> ORGANISM: Artificial Sequence
<220> FEATURE:
<223> OTHER INFORMATION: synthetically-generated primers

<400> SEQUENCE: 6
cagagtagcg aggacttgaa gag                                           23

<210> SEQ ID NO 7
<211> LENGTH: 20
<212> TYPE: DNA
<213> ORGANISM: Artificial Sequence -continued

```
<220> FEATURE:
<223> OTHER INFORMATION: synthetically-generated primers

<400> SEQUENCE: 7
cccaataggt ccagaatgtc                                                 20

<210> SEQ ID NO 8
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 8
ttttggtcct tttaaatctc                                                 20

<210> SEQ ID NO 9
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 9
ccgggaccga tccagcctcc                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 10
ggtaagtcca ccatacacac                                                 20

<210> SEQ ID NO 11
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 11
ccgggaccga tccagcctcc                                                 20

<210> SEQ ID NO 12
<211> LENGTH: 23
<212> TYPE: DNA
<213> ORGANISM: Artificial Sequence
<220> FEATURE:
<223> OTHER INFORMATION: synthetically-generated primers

<400> SEQUENCE: 12
agcactgtaa gagactatga acg                                             23

<210> SEQ ID NO 13
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 13
ctcgcctccg ccatccaccc                                                 20
```

<210> SEQ ID NO 14
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 14
cttgccagct cctgtctcac                                                    20

<210> SEQ ID NO 15
<211> LENGTH: 23
<212> TYPE: DNA
<213> ORGANISM: Artificial Sequence
<220> FEATURE:
<223> OTHER INFORMATION: synthetically-generated primers

<400> SEQUENCE: 15
atgaatacgg ctacagcaac agg                                                23

<210> SEQ ID NO 16
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 16
gagatgctca gtgttggggg                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 17
gtagaagaac ttcaggggc                                                     20

<210> SEQ ID NO 18
<211> LENGTH: 21
<212> TYPE: DNA
<213> ORGANISM: Artificial Sequence
<220> FEATURE:
<223> OTHER INFORMATION: synthetically-generated primers

<400> SEQUENCE: 18
ctgctctagt gtctccactt c                                                  21

<210> SEQ ID NO 19
<211> LENGTH: 23
<212> TYPE: DNA
<213> ORGANISM: Artificial Sequence
<220> FEATURE:
<223> OTHER INFORMATION: synthetically-generated primers

<400> SEQUENCE: 19
cgacggttgt aataagaagt ttg                                                23

<210> SEQ ID NO 20
<211> LENGTH: 19
<212> TYPE: DNA
<213> ORGANISM: Artificial Sequence
<220> FEATURE:
<223> OTHER INFORMATION: synthetically-generated primers

```
<400> SEQUENCE: 20 atgtcccttaa agtgtgtag                                                    19

<210> SEQ ID NO 21
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 21
ggaaatcata cttacctggc                                                    20

<210> SEQ ID NO 22
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 22
aaacgcagtc ccccactacc                                                    20

<210> SEQ ID NO 23
<211> LENGTH: 21
<212> TYPE: DNA
<213> ORGANISM: Artificial Sequence
<220> FEATURE:
<223> OTHER INFORMATION: synthetically-generated primers

<400> SEQUENCE: 23
ctcgacagcc caatctttgt t                                                  21

<210> SEQ ID NO 24
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 24
accaacactt ccacttagcc                                                    20

<210> SEQ ID NO 25
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 25
actcatccac cgagctact                                                     19

<210> SEQ ID NO 26
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 26
gatgccataa aggcaagaac                                                    20

<210> SEQ ID NO 27
```

```
<211> LENGTH: 22
<212> TYPE: DNA
<213> ORGANISM: Artificial Sequence
<220> FEATURE:
<223> OTHER INFORMATION: synthetically-generated primers

<400> SEQUENCE: 27
gctggttcgt ctatcttgtg gg                                              22

<210> SEQ ID NO 28
<211> LENGTH: 22
<212> TYPE: DNA
<213> ORGANISM: Artificial Sequence
<220> FEATURE:
<223> OTHER INFORMATION: synthetically-generated primers

<400> SEQUENCE: 28
cctgcactgg atgagttact tg                                              22

<210> SEQ ID NO 29
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 29
cagagaaagt agttggtaa                                                  19

<210> SEQ ID NO 30
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 30
tggtcaagct tgtaaataa                                                  19

<210> SEQ ID NO 31
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 31
acagaaaggg caacaataa                                                  19

<210> SEQ ID NO 32
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 32
gctcaaagct aaaacgaca                                                  19

<210> SEQ ID NO 33
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 33
```

```
gggctgctca gaagtctat                                                19

<210> SEQ ID NO 34
<211> LENGTH: 21
<212> TYPE: DNA
<213> ORGANISM: Artificial Sequence
<220> FEATURE:
<223> OTHER INFORMATION: synthetically-generated primers

<400> SEQUENCE: 34
aaaatcactg aaagaaacca c                                             21

<210> SEQ ID NO 35
<211> LENGTH: 26
<212> TYPE: DNA
<213> ORGANISM: Artificial Sequence
<220> FEATURE:
<223> OTHER INFORMATION: synthetically-generated primers

<400> SEQUENCE: 35
actttgcata cagtcctact ttactt                                        26

<210> SEQ ID NO 36
<211> LENGTH: 25
<212> TYPE: DNA
<213> ORGANISM: Artificial Sequence
<220> FEATURE:
<223> OTHER INFORMATION: synthetically-generated primers

<400> SEQUENCE: 36
ggaaaggaga cttgagagat gatac                                         25

<210> SEQ ID NO 37
<211> LENGTH: 24
<212> TYPE: DNA
<213> ORGANISM: Artificial Sequence
<220> FEATURE:
<223> OTHER INFORMATION: synthetically-generated primers

<400> SEQUENCE: 37
tcgatatggt ttataagagg ttgg                                          24

<210> SEQ ID NO 38
<211> LENGTH: 24
<212> TYPE: DNA
<213> ORGANISM: Artificial Sequence
<220> FEATURE:
<223> OTHER INFORMATION: synthetically-generated primers

<400> SEQUENCE: 38
gggccacgat ataggagt atgc                                            24

<210> SEQ ID NO 39
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 39
cccctgtcta tccttagcg                                                19

<210> SEQ ID NO 40
<211> LENGTH: 19
<212> TYPE: DNA
```

```
<213> ORGANISM: Artificial Sequence
<220> FEATURE:
<223> OTHER INFORMATION: synthetically-generated primers

<400> SEQUENCE: 40
actgcaccag aaacgtcag                                                        19

<210> SEQ ID NO 41
<211> LENGTH: 34
<212> TYPE: DNA
<213> ORGANISM: Artificial Sequence
<220> FEATURE:
<223> OTHER INFORMATION: synthetically-generated primers
<220> FEATURE:
<221> NAME/KEY: misc_feature
<222> LOCATION: 29
<223> OTHER INFORMATION: n = g, a, t or c
<220> FEATURE:
<221> NAME/KEY: misc_feature
<222> LOCATION: 30
<223> OTHER INFORMATION: n = g, a, t or c
<220> FEATURE:
<221> NAME/KEY: misc_feature
<222> LOCATION: 31
<223> OTHER INFORMATION: n = g, a, t or c
<220> FEATURE:
<221> NAME/KEY: misc_feature
<222> LOCATION: 32
<223> OTHER INFORMATION: n = g, a, t or c
<220> FEATURE:
<221> NAME/KEY: misc_feature
<222> LOCATION: 33
<223> OTHER INFORMATION: n = g, a, t or c
<220> FEATURE:
<221> NAME/KEY: misc_feature
<222> LOCATION: (34)...(34)
<223> OTHER INFORMATION: n = g, a, t or c

<400> SEQUENCE: 41
ctttccctac acgacgctct tccgatctnn nnnn                                       34

<210> SEQ ID NO 42
<211> LENGTH: 37
<212> TYPE: DNA
<213> ORGANISM: Artificial Sequence
<220> FEATURE:
<223> OTHER INFORMATION: synthetically-generated primers

<400> SEQUENCE: 42
caagcagaag acggcatacg agctcttccg atctggg                                    37

<210> SEQ ID NO 43
<211> LENGTH: 58
<212> TYPE: DNA
<213> ORGANISM: Artificial Sequence
<220> FEATURE:
<223> OTHER INFORMATION: synthetically-generated primers

<400> SEQUENCE: 43
aatgatacgg cgaccaccga gatctacact ctttccctac acgacgctct tccgatct            58

<210> SEQ ID NO 44
<211> LENGTH: 34
<212> TYPE: DNA
<213> ORGANISM: Artificial Sequence
<220> FEATURE:
<223> OTHER INFORMATION: synthetically-generated primers

<400> SEQUENCE: 44
caagcagaag acggcatacg agctcttccg atct                                       34
```

```
<210> SEQ ID NO 45
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 45
tctataaaat ggcggctcg                                              19

<210> SEQ ID NO 46
<211> LENGTH: 18
<212> TYPE: DNA
<213> ORGANISM: Artificial Sequence
<220> FEATURE:
<223> OTHER INFORMATION: synthetically-generated primers

<400> SEQUENCE: 46
ggaaaagatg gcggctca                                               18

<210> SEQ ID NO 47
<211> LENGTH: 19
<212> TYPE: DNA
<213> ORGANISM: Artificial Sequence
<220> FEATURE:
<223> OTHER INFORMATION: synthetically-generated primers

<400> SEQUENCE: 47
tgtctaagat ggcggaagt                                              19

<210> SEQ ID NO 48
<211> LENGTH: 20
<212> TYPE: DNA
<213> ORGANISM: Artificial Sequence
<220> FEATURE:
<223> OTHER INFORMATION: synthetically-generated primers

<400> SEQUENCE: 48
cctgccctct agtggtttct                                             20
```

RNA-YY1 INTERACTIONS

CLAIM OF PRIORITY

This application is a U.S. National Phase Application under 35 U.S.C. § 371 of International Patent Application No. PCT/US2012/045402, filed on Jul. 3, 2012, which claims the benefit of U.S. Provisional Patent Application Ser. No. 61/504,660, filed on Jul. 5, 2011, the entire contents of the foregoing are hereby incorporated by reference.

FEDERALLY SPONSORED RESEARCH OR DEVELOPMENT

This invention was made with Government support under Grant No. RO1-GM090278 awarded by the National Institutes of Health. The Government has certain rights in the invention.

TECHNICAL FIELD

This invention relates to methods for modulation of RNA-YY1 interactions, and methods for identifying compounds that modulate RNA-YY1 interactions.

BACKGROUND

Transcriptome analyses have suggested that, although only 1-2% of the mammalian genome is protein-coding, 70-90% is transcriptionally active (Carninci et al., Science 309, 1559-1563, 2005; Kapranov et al., Science 316, 1484-148, 2007; Mercer et al., Nat Rev Genet 10, 155-159, 2009). Ranging from 100 nt to >100 kb, these transcripts are largely unknown in function, may originate within or between genes, and may be conserved and developmentally regulated (Kapranov et al., 2007, supra; Guttman et al., 2009). Methods for targeting these transcripts allow for modulation of gene expression.

SUMMARY

The present invention is based, at least in part, on the discovery that YY1 protein acts as an adaptor protein that loads non-coding RNAs onto target sequences. Thus, methods and compounds targeting the YY1-RNA interaction can be used to modulate gene expression.

In one aspect, the invention provides methods for preparing a library of nuclear ribonucleic acids (nRNAs) that specifically bind YY1. Preferably, the methods include (a) contacting a sample containing nRNAs, e.g. at least $10^4$, $10^5$, or $10^6$ different nRNAs, with (i) YY1 protein and (ii) a YY1 binding agent, under conditions sufficient to form complexes between the nRNA, YY1 protein and the YY1 binding agent, and (b) isolating the complexes.

In some embodiments, the methods further include (c) synthesizing cDNA complementary to the nRNA, and (d) selecting cDNAs that (i) have RPKM above a desired threshold or (ii) are enriched compared to a control library, or both (i) and (ii).

In a further aspect, the invention provides methods for preparing a plurality of cDNAs complementary to a pool of nuclear ribonucleic acids (nRNAs). Preferably, the methods include providing a sample comprising nuclear ribonucleic acids, e.g., a sample comprising nuclear lysate, e.g., comprising nRNAs bound to nuclear proteins; contacting the sample with an agent, e.g., an antibody, that binds specifically to YY1 protein, under conditions sufficient to form complexes between the agent and YY1 proteins, e.g., such that the nRNAs remain bound to the YY1 proteins; isolating the complexes; synthesizing DNA complementary to the nRNAs to provide an initial population of cDNAs; optionally PCR-amplifying the cDNAs using strand-specific primers; purifying the initial population of cDNAs to obtain a purified population of cDNAs that are at least about 20 nucleotides (nt) in length, e.g., at least 25, 50, 100, 150 or 200 nt in length; sequencing at least part of substantially all of the purified population of cDNAs; comparing the high-confidence sequences to a reference genome, and selecting those sequences that have a high degree of identity to sequences in the reference genome, e.g., at least 95%, 98%, or 99% identity, or that have fewer than 10, 5, 2, or 1 mismatches; and selecting those cDNAs that have (i) reads per kilobase per million reads (RPKM) above a desired threshold, and (ii) are enriched as compared to a control library (e.g., a protein-null library or library made from an IgG pulldown done in parallel); thereby preparing the library of cDNAs.

In some embodiments, the methods further include a step of crosslinking the nRNAs bound to nuclear proteins, e.g., using methods known in the art, including chemical or other crosslinkers, e.g., ultraviolet irradiation.

In some embodiments of the methods described herein, the agent is an antibody and isolating the complexes comprises immunoprecipitating the complexes.

In some embodiments of the methods described herein, the cDNAs are synthesized using strand-specific adaptors.

In some embodiments, the methods described herein include sequencing substantially all of the cDNAs.

In a further aspect, the invention provides libraries of cDNAs complementary to a pool of nuclear ribonucleic acids (nRNAs) prepared by a method described herein. In some embodiments, each of the cDNAs is linked to an individually addressable bead or area on a substrate.

In a further aspect, the invention provides methods for identifying compounds that disrupts binding of one or more long non-coding RNAs (lncRNAs) to YY1 protein. Preferably, the methods include providing a sample comprising a lncRNA and YY1, wherein the lncRNA can bind to the YY1 and form lncRNA-YY1 complexes; contacting the sample with a test compound; and detecting the formation of lncRNA-YY1 complexes in the presence and the absence of the test compound, wherein a decrease in formation of lncRNA-YY1 complexes in the presence of the test compound as compared to formation of lncRNA-YY1 complexes in the absence of the test compound indicates that the test compound disrupts binding of the lncRNA to YY1.

In some embodiments of the methods described herein, the sample is a cell-free sample. In some embodiments, the sample comprises a cell expressing the lncRNA and YY1. In some embodiments, the sample is from a mammalian cell, e.g., a human cell or a non-human animal cell, e.g., a non-human primate, cow, pig, sheep, horse, cat, dog, or other domestic or agricultural animal.

In some embodiments of the methods described herein, the YY1, the lncRNA, or both, is labeled.

In some embodiments, the test compound is a nucleic acid, e.g., an antagomir, mixmer, or gapmer of LNA.

In some embodiments, the methods described herein further include isolating lncRNA-YY1 complexes from the sample, and optionally isolating unbound YY1 from the sample, e.g., by contacting the sample with an anti-YY1 antibody, and isolating lncRNA-YY1-antibody complexes and unbound YY1.

In some embodiments, the methods further include selecting a compound that disrupts binding of the lncRNA to YY1; contacting a tumor cell with the compound; measuring proliferation, survival, or invasiveness of the tumor cell in the presence and absence of the compound; and identifying as a candidate therapeutic compound a compound that inhibits proliferation, affects survival, e.g., induces or promotes cell death, or reduces or delays metastasis, of the tumor cell.

In some embodiments, the methods further include administering the candidate compound to an animal model of cancer, and detecting an effect of the compound on cancer in the animal model, e.g., an effect on tumor size or metastasis.

In a further aspect, the invention provides methods for identifying an RNA target for the treatment of cancer, the method comprising: (a) comparing (i) a library of nRNAs that specifically bind YY1 prepared from a normal cell with (ii) a library of nRNAs that specifically bind YY1 prepared from a cancerous cell, wherein the normal cell and cancerous cell are of the same tissue type; and (b) identifying an nRNA that is differentially expressed between the libraries of (a)(i) and (a)(ii) as an RNA target for treatment of cancer.

In a further aspect, the invention provides methods for identifying a therapeutic target for the treatment of cancer, the method comprising: providing a population of nRNAs from a first cell type, by:
(1) providing a sample comprising nuclear ribonucleic acids, e.g., a sample comprising nuclear lysate, e.g., comprising nRNAs bound to nuclear proteins, from the first cell type;
   contacting the sample with an agent, e.g., an antibody, that binds specifically to YY1 protein, under conditions sufficient to form complexes between the agent and YY1 proteins, e.g., such that the nRNAs remain bound to the YY1 proteins;
   isolating the complexes; and
   thereby providing a population of nRNAs from the first cell type;
(b) providing a population of nRNAs from a second cell type, by:
(1) providing a sample comprising nuclear ribonucleic acids, e.g., a sample comprising nuclear lysate, e.g., comprising nRNAs bound to nuclear proteins, from the second cell type;
   contacting the sample with an agent, e.g., an antibody, that binds specifically to YY1 protein, under conditions sufficient to form complexes between the agent and YY1 proteins, e.g., such that the nRNAs remain bound to the YY1 proteins;
   isolating the complexes;
   synthesizing DNA complementary to the nRNAs to provide an initial population of cDNAs;
(2) thereby providing a population of cDNAs from the second cell type;
(c) wherein the first and second cell types are from the same type of tissue, and the first or second cell type is a tumor cell;
(d) contacting the population of nRNAs from the first cell type with the cDNAs from the second cell type, under conditions sufficient for the nRNAs to bind to complementary cDNAs; and
(e) identifying an nRNA that is differentially expressed in the first or second cell type as a therapeutic target for the treatment of cancer.

As used herein, "YY1" refers to transcriptional repressor protein YY1, the human homolog of which has a nucleic acid sequence as set forth in the GenBank database at NM_003403.3→NP_003394.1

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

1A. Map of Xist and transgenes. M, MluI; R, RsrII; N, NheI; P, PmlI.

1B. qRT-PCR of Xist in wildtype female MEF (WT) and two X-FP clones. Transgenic RNA quantitated at uXist; total Xist at Exons 1-3. Xist levels normalized to WT (set arbitrarily to 1.0). Averages±1 standard deviation (SD) from three independent experiments shown.

1C. Xist qRT-PCR measured at Exons 1-3.

1D. qRT-PCR of transgenic Xist for X-RF(7) and X-RARF(10). Levels at Dox 0 h set to 1.0.

1E. qRT-PCR of endogenous (uRA) and total (exons 1-3) Xist in X-RA clones.

Figure 2A:
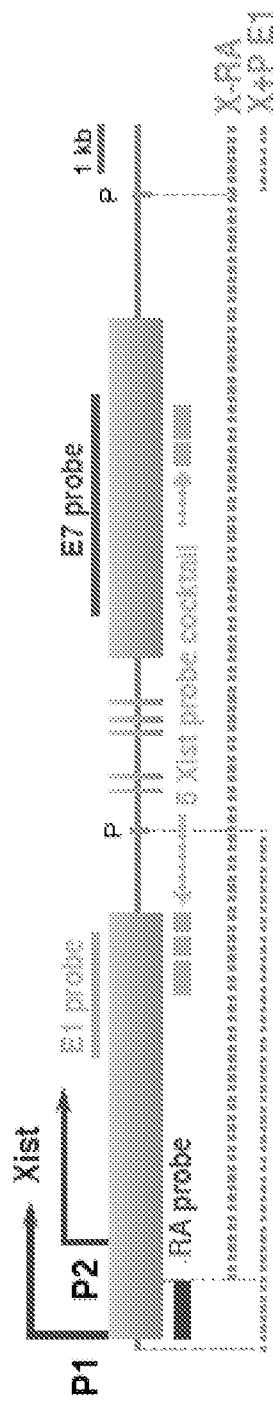
Figure 2B:
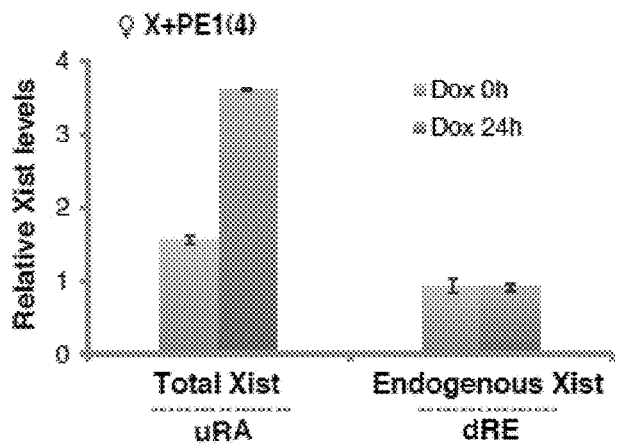

FIGS. 2A-B. Autosomal transgenes attract Xist RNA way from Xi.

2A. Map of Xist, FISH probes, and transgenes. P, PasI.

2B. qRT-PCR for total (uRA) and endogenous (dRE) Xist.

FIGS. 3A-E. YY1 protein is required for Xist localization.

3A. Map of the proximal 2-kb region of Xist. One CTCF and three putative YY1 binding sites near Repeat F are shown.

3B. Western blot and qRT-PCR 48 hours after Ctcf knockdown using C1 or C3 siRNA. Averages±SD of three independent experiments shown.

3C. YY1 Western blot and Yy1/Xist qRT-PCR after Yy1 knockdown using Y1 or Y2 siRNA. Averages±SD from 7 independent experiments shown for qRT-PCR. One representative Western blot shown.

3D. Xist FISH after Yy1 knockdown. Cells with pinpoint or no Xist were scored negative. Averages±SD from 206-510 nuclei/sample from three independent experiments.

3E. H3K27me3 immunostaining followed by Xist RNA FISH in Yy1-knockdown cells. Histogram shows counts (n=62-138).

Figure 4A:
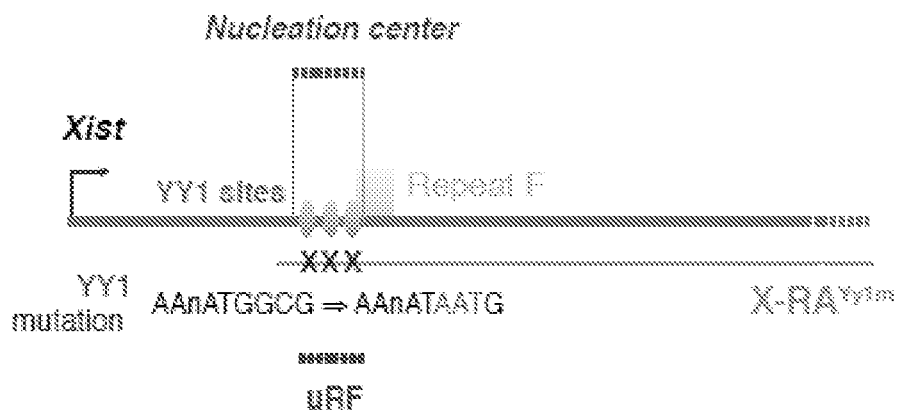
Figure 4B:
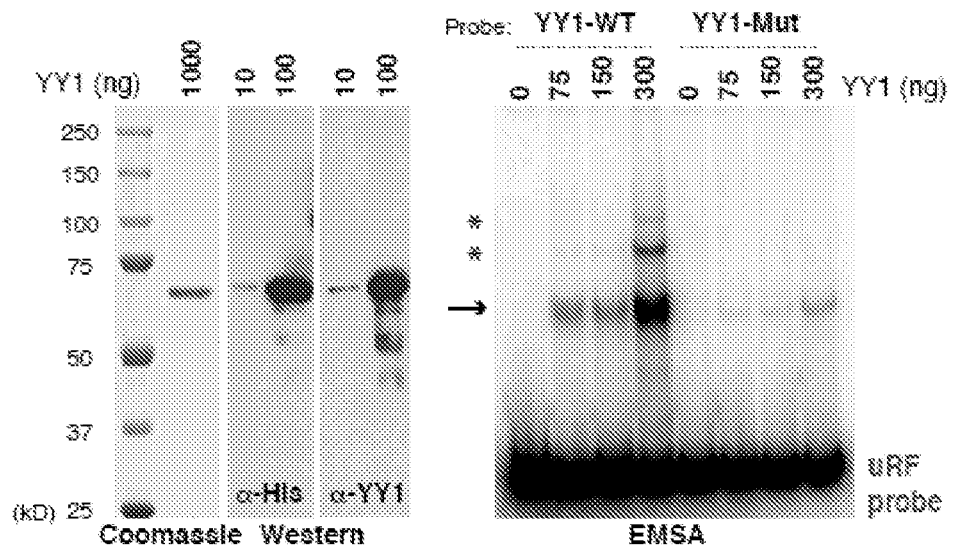
Figure 4C:
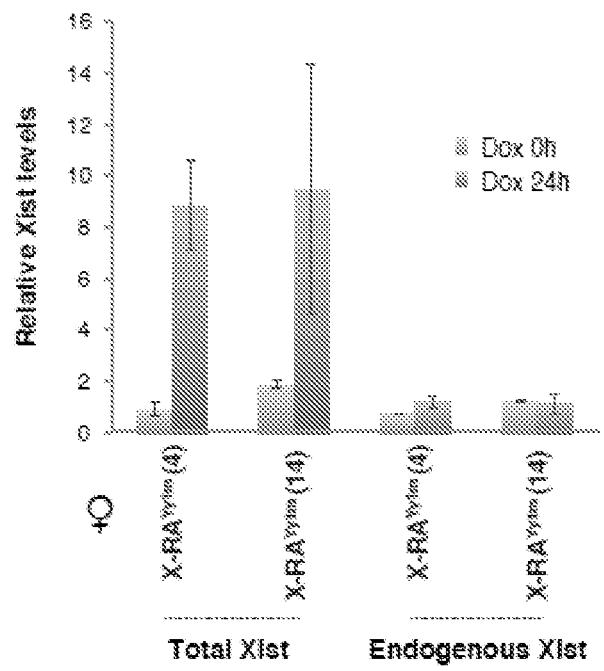

FIGS. 4A-C. Mutating YY1-binding sites in the DNA abolishes Xist RNA loading

4A. Map of proximal Xist, YY1-binding sites, transgenes, and EMSA probe. Site-directed mutation of YY1 sites shown.

4B. Left panels: SDS-PAGE, Coomassie staining, and Western blot of purified recombinant His-YY1 protein. Right panel: EMSA using YY1 and a 280-bp uRF probe. WT, wildtype YY1 probe. Mut, mutated YY1 probe. Arrow, YY1-uRF shift. Asterisks, increasing Yy1 occupancy on uRF probe.

4C. qRT-PCR of total (Exons 1-3) and endogenous (uRA) Xist in female X-RA$^{Yy1m}$ cells.

Figure 5A:
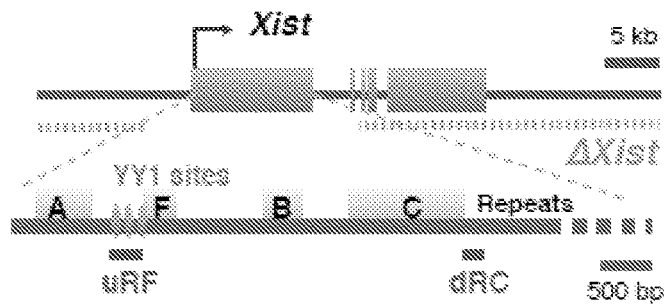
Figure 5B:
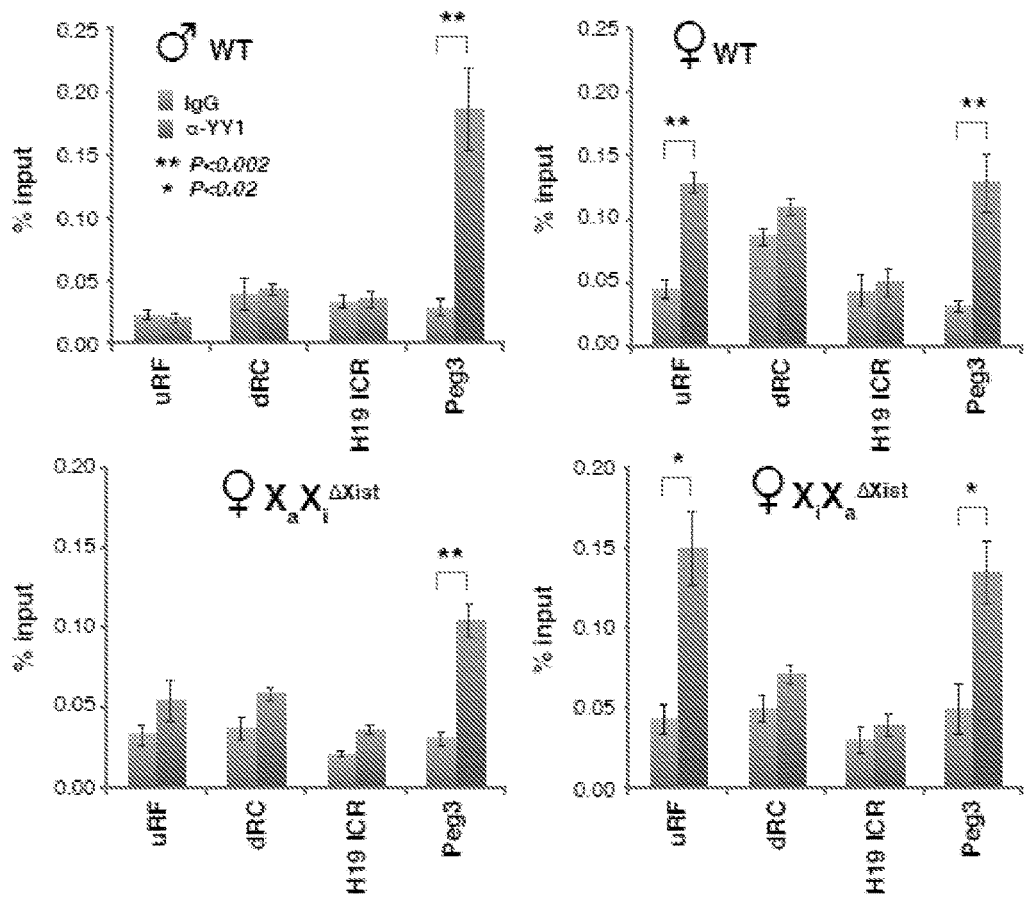
Figure 5C:
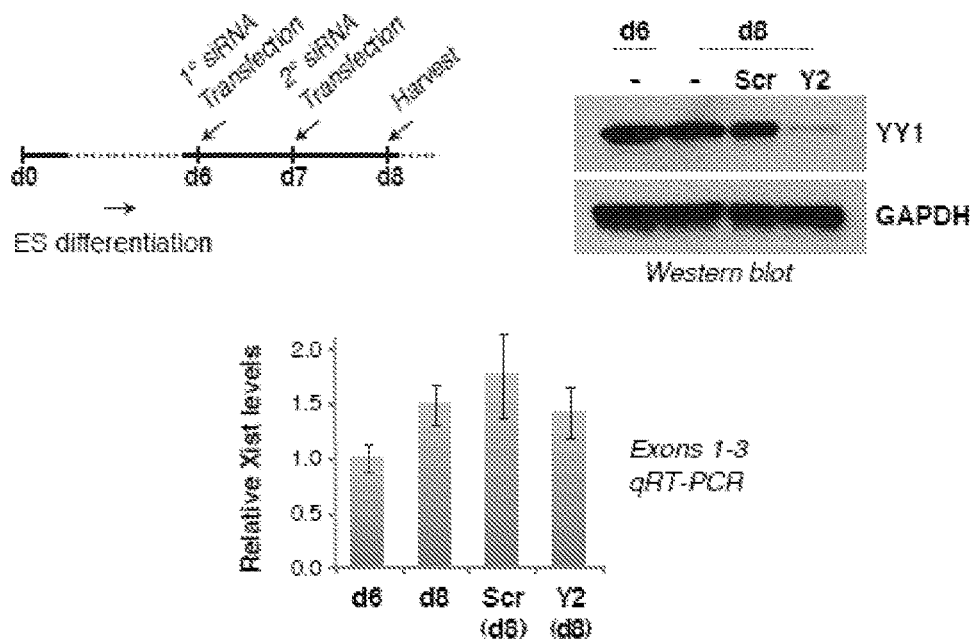

FIGS. 5A-C. Xi-specific YY1 binding in MEFs and ES cells.

5A. Map of the Xist deletion in MEF lines (Csankovszki et al., 1999; Zhang et al., 2007), ChIP-PCR amplicons, and YY1 sites.

5B. YY1 ChIP analyses in indicated cell lines. At least three independent experiments performed for each cell line. Averages±standard errors (SE) from at least 3 independent experiments shown. Statistical significance, P, determined by the Student t-test (asterisks).

5C. YY1 knockdown in differentiating female ES cells (Tsix$^{TST/+}$) via the indicated timeline. Cells were split into siRNA-treated and -untreated samples on day 6 (d6). Western blot showed good knockdown. Xist qRT-PCR showed constant steady state levels; averages±SD from three independent knockdown experiments shown.

FIGS. 6A-F. YY1 is an RNA-binding protein that bridges Xist and chromatin.

6A. Map of Xist, transgenes, and RT-PCR amplicons.

6B. UV-crosslink RIP of female MEFs, followed by qRT-PCR for Xist (dRC, Exons 1-3) or RNA controls (U1 snRNA, Gapdh). Samples were precipitated with YY1 antibodies or IgG. 1% input used. -UV and -RT controls performed in parallel. Left panel, EtBr-stained gel. Right panel, RT-PCR quantitation. Averages±SE of 3 independent experiments.

6C. RNA pulldown assay using purified His-YY1 or His-GFP (Western blot) and WT female ES RNA. RT-PCR quantitation shown at 3 different Xist positions (uRF, uRA, dRE) and two controls (Gadph, α-tubulin). Averages of 5 independent experiments±SE.

6D. RNA pulldown assay using RNAs from transgenic lines after dox induction. qRT-PCR performed at dRC. Averages±SE for 3 independent experiments.

6E. RNA pulldown assay using equal molar amounts of in vitro-transcribed RNA fragments AF (2.5 kb), BC (2.5 kb), eE1 (2.5 kb), B (1.2 kb), and C (1.8 kb) as illustrated in the map. Quantitated by qRT-PCR. 20% of input shown on the gel. P calculated using t-test. B, BamHI; E, EcoRI; Bs, BstBI; S, ScaI. Averages of 2 independent experiments±SE.

6F. Schematic diagram showing that YY1 contacts Xist RNA and DNA via different nucleic acid motifs.

DETAILED DESCRIPTION

The experiments described herein elucidate how Xist RNA loads onto Xi and establishes its action in cis. This work identifies its primary loading site—dubbed the 'nucleation center'—and shows that bound YY1 proteins trap the Xist silencing complex before it can translocate in cis along Xi. A most surprising observation, however, is that Xist RNA is not inherently cis-acting. The RNA freely diffuses and trans-migrates between any chromosome bearing an open loading site. These discoveries imply that Xist RNA is not irreversibly bound to chromatin and that, when displaced from chromatin, the RNA remains stable and free to act in trans. Thus, the RNA's selective action on Xi cannot only be the result of Xi-specific transcription, but must also be the consequence of allele-specific binding of YY1 to the nucleation center. Even so, YY1 alone cannot specify the Xi fate, as Xist does not nucleate at any other of a large number of genome-wide YY1-bound sites. YY1 and as yet undefined accessory factors—such as lncRNAs like Tsix which are specific to X—may conspire to define the nucleation center.

Figure 6A:
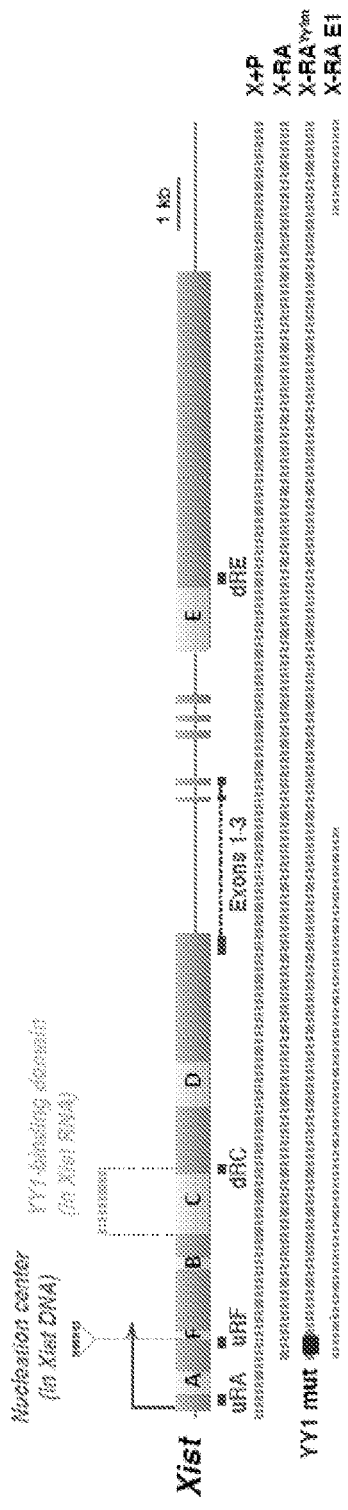
Figure 6B:
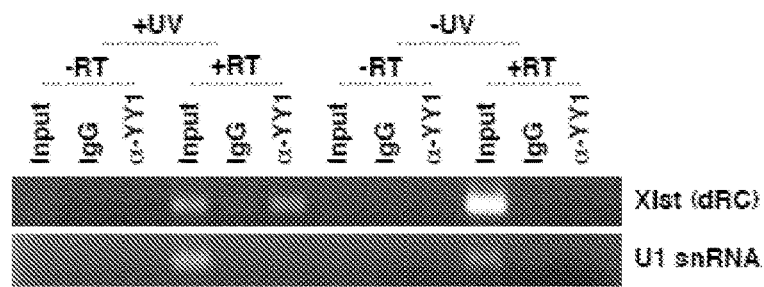
Figure 6B:
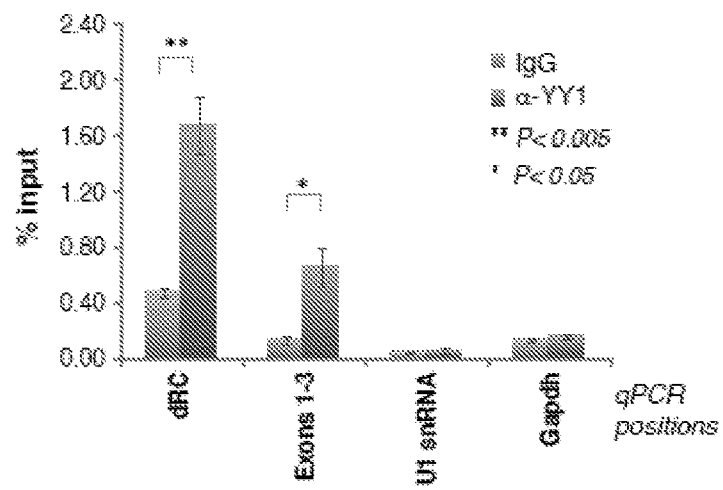
Figure 6C:
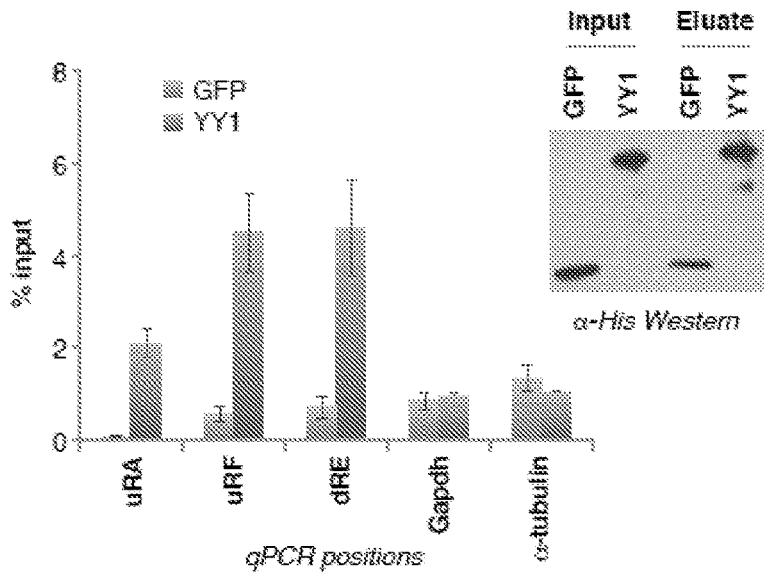
Figure 6D:
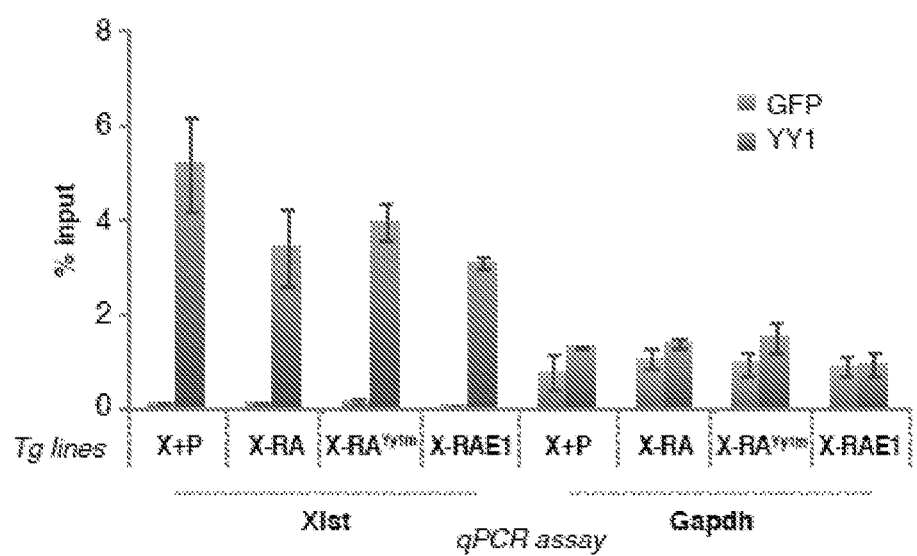
Figure 6E:
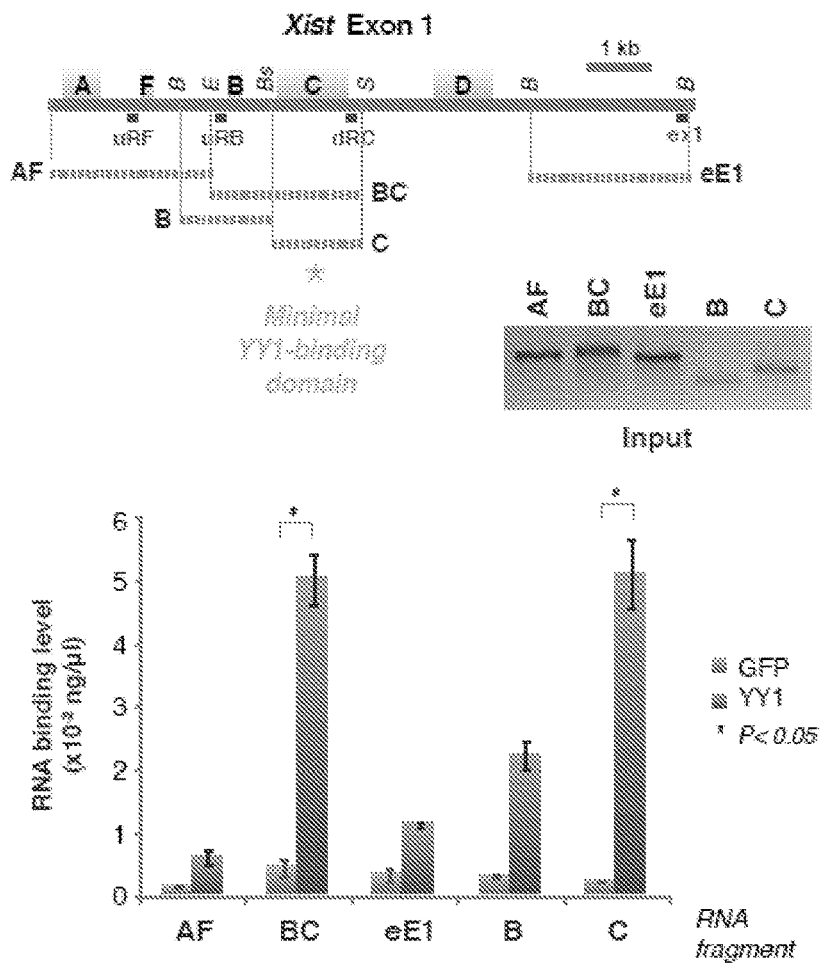
Figure 6F:
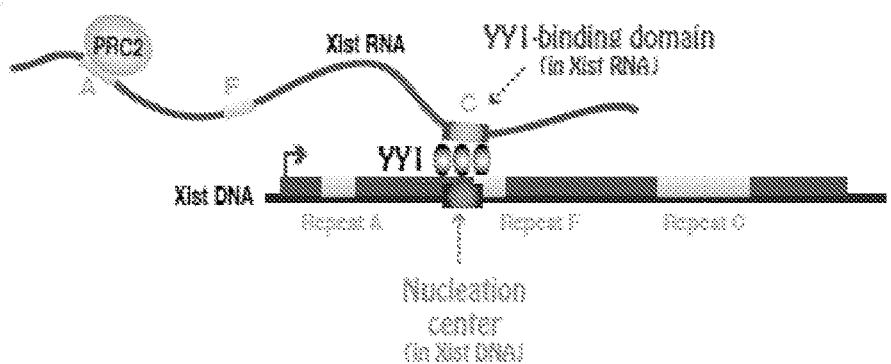

Importantly, YY1 binds both DNA and RNA. Specific YY1-DNA contacts are required to formulate the nucleation center, and specific YY1-RNA interactions are necessary to load Xist particles (FIG. 6F). YY1 is therefore a bivalent protein that bridges regulatory long ncRNA and its chromatin target. Its zinc fingers may mediate the interaction with both DNA and RNA, as some zinc finger proteins can bind RNA as well as DNA in vitro (Iuchi, 2001). Interestingly, although YY1 binds the AAnATGCG motif on DNA, its interaction with Xist RNA does not occur through the corresponding motif on the RNA. Instead it contacts Xist RNA via Repeat C, a C-rich repeat unique to Xist and one of the best-conserved elements within eutherian Xist/XIST (Brockdorff et al., 1992; Brown et al., 1992). A recent study has shown that targeting Repeat C and an adjacent exon 1 sequence using locked nucleic acids (LNAs) causes rapid Xist displacement from Xi (Sarma et al., 2010). Given that Repeat C is the YY1-binding domain of Xist RNA, one possibility is that the LNA inhibited crucial interactions between Xist and the YY1 receptor. This work shows that Repeat A is not required. It was previously reported that human XIST without the Repeat A region cannot localize properly (Chow et al., 2007); however, the deletion removed not only Repeat A but also three of eight clustered YY1 sites, which could therefore compromise the nucleation center. The data demonstrate that Xist RNA's interactions with two proteins are crucial for XCI: EZH2 (PRC2) via Repeat A to form the silencing complex, and YY1 via Repeat C to load onto the nucleation center (FIG. 6F).

The data have implications for Polycomb regulation. Because the PRC2 subunits, EED, EZH2, SUZ12, and RBAP48, lack sequence-specific DNA binding subunits, cis-acting long ncRNAs have been proposed as locus-specific recruiting tools (Zhao et al., 2008; Lee, 2009, 2010). The concept of YY1 as docking protein is intriguing, given that the related protein, PHO, has been proposed to recruit Polycomb complexes in fruit flies (Ringrose and Paro, 2004; Schwartz and Pirrotta, 2008). Mammalian YY1 has been implicated as a binding partner for PRC2 (Atchison et al., 2003; Wilkinson et al., 2006; Ku et al., 2008). This idea has been debated, however, as YY1 has not generally co-purified with PRC2 (Kuzmichev et al., 2002; Landeira et al., 2010; Li et al., 2010), mutating YY1 sites in HOX-D does not abrogate PRC2 binding (Woo et al., 2010), and YY1 motifs are not enriched near PRC2-binding sites (Mendenhall et al., 2010). Nevertheless, this work demonstrates that YY1 is required for Xist loading and, by inference, for Polycomb recruitment in the context of XCI.

RIP-Seq—Methods of Producing Long Non-Coding RNAs

Described herein are methods for producing libraries of lncRNAs that bind to YY1. In some embodiments, the methods include the steps shown in FIG. 1A; one of skill in the art will appreciate that other techniques can be substituted for those shown.

In some embodiments, the methods include providing a sample comprising nuclear ribonucleic acids (nRNAs) bound to YY1; and contacting the sample with an agent, e.g., an antibody, that binds specifically to YY1, under conditions and for a time sufficient to form complexes between the agent and the protein; isolating the complexes; synthesizing DNA complementary to the nRNAs to provide an initial population of cDNAs; PCR-amplifying, if necessary, using strand-specific primers; purifying the initial population of cDNAs to obtain a purified population of cDNAs that are at least 20 nucleotides (nt) in length; high-throughput sequencing the purified population of cDNAs. Homopolymer reads are filtered, and reads matching the mitochondrial genome and ribosomal RNAs are excluded from all subsequent analyses. Reads that align to a reference genome with ≤1 mismatch are retained, excluding homopolymers, reads that align to the mitochondrial genome, and ribosomal RNAs. High probability YY1-interacting transcripts are then called based on two criteria: (1) that the candidate transcript has a minimum read density in RPKM terms (number of reads per kilobase per million reads); (2) that the candidate transcript is enriched in the wildtype library versus a suitable control library (such as a protein-null library or library made from an IgG pulldown done in parallel).

In general, to construct RIP-seq libraries, cell nuclei are prepared, treated with DNAse, and incubated with antibodies directed against a chromatin-associated factor of interest, along with a control IgG reaction in parallel. RNA-protein complexes are then immunoprecipitated with agarose beads, magnetic beads, or any other platform in solution or on a solid matrix (e.g., columns, microfluidic devices). RNAs are extracted using standard techniques. To capture all RNAs (not just polyA RNAs) and to preserve strand information, asymmetric primers are used to generate cDNA from the RNA template, in which the first adaptor (adaptor1) to make the first strand cDNA contains a random multimer sequence (such as random hexamers) at the 3' end. A reverse transcriptase is used to create the first strand. A distinct second adaptor (adaptor2) is used to create the second strand. One example is as follows: If Superscript II is used, it will add non-template CCC 3' overhangs, which can then be used to hybridize to a second adaptor containing GGG at the 3' end, which anneal to the non-template CCC overhangs. Other methods of creating second strands may be substituted. PCR using adaptor1- and adaptor2-specific primer pairs is then the performed to amplify the cDNAs and the products sequenced via standard methods of high throughput sequencing. Prior to sequencing, a size-selection step can be incorporated (if desired) in which RNAs or cDNAs of desired sizes are excised after separation by gel electrophoresis (e.g., on a NuSieve agarose gel or in an acrylamide gel) or other methods of purification, such as in a microfluidic device or in standard biochemical columns.

YY1-Binding lncRNAs and lncRNA Libraries

The present invention includes libraries of lncRNAs produced by methods described herein. In some embodiments, the libraries are in solution, or are lyophilized. In some embodiments, the libraries are bound to a substrate, e.g., wherein each member of the library is bound to an individually addressable member, e.g., an individual area on an array (e.g., a microarray), or a bead.

In one embodiment, a lncRNA includes a nucleotide sequence that is at least about 85% or more homologous to the entire length of a lncRNA sequence shown herein, e.g., in Table 2, 3, 4, or 5, or a fragment comprising at least 20 nt thereof (e.g., at least 25, 30, 35, 40, 50, 60, 70, 80, 90, or 100 nt thereof, e.g., at least 5%, 10%, 15%, 20%, 25%, 30%, 35%, 40%, 50% or more of the full length lncRNA). In some embodiments, the nucleotide sequence is at least about 90%, 91%, 92%, 93%, 94%, 95%, 96%, 97%, 98%, 99% or 100% to a lncRNA sequence shown herein. In some embodiments, the nucleotide sequence is at least about 85%, e.g., is at least about 90%, 91%, 92%, 93%, 94%, 95%, 96%, 97%, 98%, 99% or 100% homologous to a lncRNA sequence described herein in a region that is much more conserved but has lower sequence identity outside that region.

LncRNAs may be functionally conserved without being highly conserved at the level of overall nucleotide identity. For example, mouse Xist shows only 76% overall nucleotide identity with human XIST using sliding 21-bp windows, or an overall sequence identity of only 60%. However, within specific functional domains, such as Repeat A, the degree of conservation can be >70% between different mammalian species. The crucial motif in Repeat A is the secondary structures formed by the repeat. For YY1-Xist interactions, the crucial motif is Repeat C, which has a similar degree of conservation between mammalian species. Other lncRNAs interacting with YY1 may therefore be similarly low in overall conservation but still have conservation in secondary structure within specific domains of the RNA, and thereby demonstrate functional conservation with respect to recruitment of YY1.

Calculations of homology or sequence identity between sequences (the terms are used interchangeably herein) are performed as follows.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

There are several potential uses for the lncRNAs described herein in the YY1 transcriptome: The RNAs themselves, or antagomirs and small molecules designed against them, can be utilized to modulate expression (either up or down) of YY1 target genes. In addition, the lncRNAs can be used in methods of detecting or identifying cancerous cells, as described herein.

Methods of Detecting Cancer

YY1 expression is altered in cancerous cells (see, e.g., Lee et al., Oncogene. "Yin Yang 1 positively regulates BRCA1 and inhibits mammary cancer formation." 2011 Jun. 13 (doi: 10.1038/onc.2011.217); Zaravinos and Spandidos, Cell Cycle. 2010 Feb. 1; 9(3):512-22; Wang et al., Expert Opin Ther Targets. 2006 April; 10(2):253-66; Castellano et al., Cell Cycle. 2009 May 1; 8(9):1367-72. Epub 2009 May 26). Libraries of YY1-binding lncRNAs described herein, and nucleic acids targeting them, can be used to detect modulated gene expression in a cell, e.g., a cancer cell. The cells can be, e.g., from a subject who has cancer, e.g., tumor cells or cells suspected of being tumor cells.

These methods can be used to diagnose cancer a subject by detecting the presence of differential expression of YY1-binding lncRNAs in a suspected cancer cell versus a normal cell, e.g., a cell from the same subject, e.g., from the same tissue in the same subject. The presence of differential expression indicates the presence of cancer in the subject.

These methods can also be used to identify lncRNAs that are differentially expressed in cancer cells versus normal cells; once identified, those lncRNAs can be targeted to alter the proliferative state of the cell. Thus the methods described herein can be used to identify therapeutic targets for the treatment of cancer; the lncRNAs can be targeted using antagomirs, antisense, siRNA and other inhibitory nucleic acids, e.g., as described in U.S. Provisional Patent Application No. 61/425,174.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease. With respect to cancer, treating includes inhibiting tumor cell proliferation, increasing tumor cell death or killing, inhibiting rate of tumor cell growth or metastasis, reducing size of tumors, reducing number of tumors, reducing number of metastases, increasing 1-year or 5-year survival rate.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung (e.g. small cell, non-small cell, squamous, adenocarcinoma), breast, thyroid, lymphoid, gastrointestinal, genito-urinary tract, kidney, bladder, liver (e.g. hepatocellular cancer), pancreas, ovary, cervix, endometrium, uterine, prostate, brain, as well as adenocarcinomas which include malignancies such as most colon cancers, colorectal cancer, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Methods of Screening

Included herein are methods for screening test compounds, e.g., polypeptides, polynucleotides, inorganic or organic large or small molecule test compounds, to identify agents useful in the treatment of cancer.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

In some embodiments, the test compounds are nucleic acids, e.g., one or more nucleic acids that have identity to all or a portion of the YY1-binding RNA, or a set of randomly generated oligos. The oligos can be LNAs, and can be antagomirs, mixmers, or gapmers.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cancer cell, and one or more effects of the test compound is evaluated. In a cultured cancer cell for example, the ability of the test compound to inhibit proliferation or affect survival, e.g., to induce or promote cell death, is evaluated.

In some embodiments, the test sample is, or is derived from (e.g., a sample taken from) a tumor, e.g., a primary or cultured tumor cell.

Methods for evaluating each of these effects are known in the art. For example, assays of proliferation or cell survival/viability are well known in the art.

A test compound that has been screened by a method described herein and determined to inhibit proliferation or affect survival, e.g., induce or promote cell death, can be considered a candidate compound. A candidate compound that has been screened, e.g., in an in vivo model of a disorder, e.g., a xenograft model, and determined to have a desirable effect on the disorder, e.g., on growth or metastasis of a tumor, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that inhibit proliferation or affect survival, e.g., induce or promote cell death) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating cancer. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a tumor, e.g., a xenograft model, as known in the art. The animal can be monitored for a change in the disorder, e.g., for an improvement in a parameter of the disorder, e.g., a parameter related to clinical outcome. In some embodiments, the parameter is tumor size, and an improvement would be a reduction or stabilization of tumor size, or a reduction in growth rate; in some embodiments, the parameter is invasiveness, and an improvement would be a reduction or delay in metastasis.

EXAMPLES

The invention is further described in the following examples, which do not limit the scope of the invention described in the claims.

Example 1. Identification of an X-Inactivation Nucleation Center and YY1 as Receptor for Xist RNA The present Example describes experiments performed to identify proteins involved in X-inactivation nucleation.

Experimental Procedures

The following materials and methods were used in the present Example.

Transgene Constructs

Figure 1A:
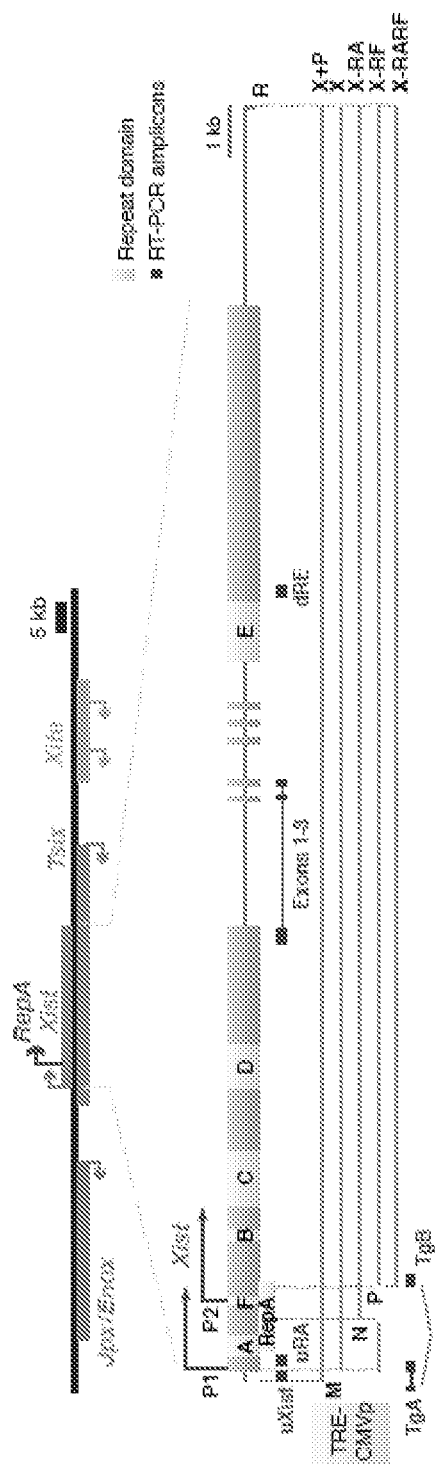
FIGS. 1A-E. Newly introduced Xist transgenes squelch Xist RNA from Xi in MEFs.

Transgenes were constructed by modifying an Xist plasmid, pSx9. Xist inserts were generated by PCR and replaced the corresponding region in pSx9 by digesting with SalI and PmlI. All constructs were put into the doxycycline-inducible system, pTRE2hyg (Clontech). Enzyme sites used for deletions are indicated in FIG. 1A. 3' truncations were generated by excising a 13.5-kb PasI fragment from transgenes. For X-RA$^{YY1m}$, YY1 binding sites were altered with QuikChange® Multi Site-Directed Mutagenesis Kit (Stratagene).

Cell Lines

Xist deletion fibroblasts (XaXi$^{\Delta\Delta Xist}$ and XiXa$^{\Delta\Delta Xist}$) and Tsix$^{TST}$/+ cells have been described (Zhang et al., 2007; Ogawa et al., 2008). For the tet-inducible system, rt-TA expressing fibroblasts were isolated from 13.5-dpc Rosa26-M2rtTA$^{+/-}$ embryos (Hochedlinger et al., 2005), immortalized with SV-40 large T-antigen, and cloned by limiting dilution. Ploidy was checked by metaphase analysis and X-painting. One male and one female clone was used for further analysis. To generate transgenic MEF lines, 15 µg of linearized transgene DNA was introduced into ~4×10$^6$ cells by electroporation (200 V, 1,050 µF), selected in 250 µg/ml hygromycin B, and clones were picked after 2 weeks. Autosomal integration was confirmed by DNA FISH.

RNA FISH, DNA FISH, and Immunostaining

Experiments were performed as described (Zhang et al., 2007) with minor changes. Xist RNA was detected using an Xist-riboprobe cocktail unless indicated. RA, E1, E7, and the transgene-specific probe, pSacBII, were labeled by nick translation (Roche). For immunostaining, cells were blocked with PBS containing 0.3% Tween20 and 3% BSA for 15 minutes before primary antibody incubation. H3K27me3 antibodies were from Active Motif (#39535). DNA FISH combined with RNA FISH or immunostaining was performed as follows: RNA FISH or immunostaining was performed first. Images were captured and their positions recorded on a Nikon Eclipse 90i microscope workstation with Volocity software (Improvision). Slides were then re-fixed in 4% paraformaldehyde, treated with RNaseA to remove RNA signals, and denatured for DNA FISH. After overnight hybridization at 37° C., slides were re-imaged at recorded positions.

Quantitative RT-PCR

Total RNA was isolated using TRIzol® (Invitrogen) and treated with TURBO DNase (Ambion). 500 ng of RNA was reverse-transcribed with random primers (Promega) using Superscript® III reverse transcriptase (Invitrogen). Control reactions without reverse transcriptase (−RT) were also prepared. qRT-PCR was performed using iQ SYBR Green Supermix (Bio-Rad) on the CFX96™ system (Bio-Rad). For each primer pair, a standard curve was generated using serial 10-fold dilutions of a plasmid containing the corresponding DNA. Copy numbers of PCR products were determined by comparison to these standard curves. Melting curve analyses showed a single peak for each primer pair, suggesting homogeneity of PCR products. Expression levels were normalized to either a-Tubulin or Gapdh levels. Primer pairs were: uXist F: 5'-TTATGTGGAAGTTCTACATAAACG-3', R: ACCGCACATCCACGGGAAAC; uRA F: CGGTTCT-TCCGTGGTTTCTC, R: GGTAAGTCCACCATACACAC; Exons 1-3 F: GCTGGTTCGTCTATCTTGTGGG, R: CAGAGTAGCGAGGACTTGAAGAG; dRE F: CCCAATAGGTCCAGAATGTC, R: TTTTGGTCCTTT-TAAATCTC; Tg-A F: CCGGGACCGATCCAGCCTCC, R: GGTAAGTCCACCATACACAC; Tg-B F: CCGGGAC-CGATCCAGCCTCC, R: AGCACTGTAAGAGACTAT-GAACG; α-tubulin F: CTCGCCTCCGCCATCCACCC, R: CTTGCCAGCTCCTGTCTCAC; Gapdh F: ATGAATACG-GCTACAGCAACAGG, R: GAGATGCTCAGTGT-TGGGGG; Ctcf F: GTAGAAGAACTTCAGGGGGC, R: CTGCTCTAGTGTCTCCACTTC; Yy1 F: CGACGGTTG-TAATAAGAAGTTTG, R: ATGTCCCTTAAGTGTGTAG; U1 snRNA F: GGAAATCATACTTACCTGGC, R: AAACGCAGTCCCCCACTACC; uRF-A F: CTCGACA-GCCCAATCTTTGTT, R: ACCAACACTTCCACT-TAGCC; uRB F: ACTCATCCACCGAGCTACT, R: GAT-GCCATAAAGGCAAGAAC; ex1 F: GCTGGTTCGTCTATCTTGTGGG, R: CCTGCACTG-GATGAGTTACTTG.

siRNA Transfection siRNAs (Integrated DNA Technologies) were sequences were: C1, 5'-CAGAGAAAGTAGTTGGTAA-3'; C3, TGGTCAAGCTTGTAAATAA; Y1, ACA-GAAAGGGCAACAATAA; Y2, GCTCAAAGCTAAAAC-GACA. Control siRNA was purchased from Invitrogen (#12935-200). Cells were transfected with siRNAs at a final concentration 20 nM using Lipofectamine™ RNAiMAX (Invitrogen). For both CTCF and YY1 depletion, transfections were performed twice at 24-hr intervals before cells were collected at indicated timepoints. Knockdown was confirmed with RT-PCR, immunostaining, or Western blotting. Most analyses were performed 48 hrs after transfection when cell growth rates and viabilities of knockdown cells were comparable to that of control. CTCF and YY1 antibodies were from Cell Signaling Technology (#2899) and Santa Cruz Biotechnology (sc-7341), respectively.

Chromatin Immunoprecipitation (ChIP)

Experiments were performed as described (Takahashi et al., 2000) with a few modifications. Approximately $2\times10^6$ cells and 2 µg of antibodies were used per ChIP. Before incubating with antibodies, chromatin was treated with 0.2 µg/µl of RNaseA at 37° C. for 30 min. Chromatin-antibody complexes were collected with Dynabeads® Protein G (Invitrogen). YY1 antibodies for ChIP were from Santa Cruz (sc-1703). Primer pairs used for qPCR were: uRF-B F: GGGCTGCTCAGAAGTCTAT, R: AAAATCACT-GAAAGAAACCAC; dRC F: ACTTTGCATACAGTC-CTACTTTACTT, R: GGAAAGGAGACTTGAGAGAT-GATAC; H19 ICR F: TCGATATGGTTTATAAGAGGTTGG, R: GGGCCACGA-TATATAGGAGTATGC; Peg3 F: CCCCTGTCTATCCT-TAGCG, R: ACTGCACCAGAAACGTCAG.

Electrophoretic Mobility Shift Assay (EMSA)

Recombinant His-YY1 protein was purified as described (Shi et al., 1991) except that it was eluted with 250 mM imidazole. For EMSA, 10 fmoles of 5'-end-labeled probes were incubated with 75-300 ng of purified YY1. Binding reactions were carried out for 30 min at room temperature in a final volume of 200 containing 10 mM Tris-HCl (pH 8.0), 5 mM $MgCl_2$, 0.2 mM $ZnCl_2$, 2 mM DTT, 150 mM NaCl, 1 µg poly(dI·dC), 0.1 mg/ml BSA, and 10% glycerol. Complexes were electrophoresed in a 4% acrylamide gel in TBE.

RNA Immunoprecipitation (RIP)

$1\times10^7$ female MEFs per IP were UV-crosslinked at 254 nm (200 $J/m^2$) in 10 ml ice-cold PBS and collected by scraping. Cells were incubated in lysis solution (0.5% NP40, 0.5% sodium deoxycholate, 400 U/ml RNase Inhibitor (Roche), and protease inhibitor cocktail (Sigma) in PBS pH 7.9) at 4° C. for 25 minutes with rotation, followed by the first DNase treatment (30 U of TURBO DNase, 15 minutes at 37° C.). After centrifugation, the supernatant was incubated with 5 µg of either IgG or YY1 antibodies immobilized on Dynabeads® Protein G, overnight at 4° C. Beads were washed three times with PBS containing 1% NP40, 0.5% sodium deoxycholate and additional 150 mM NaCl (total 300 mM NaCl) before the second DNase treatment (10 U) for 30 min. After washing another three times with the same wash buffer supplemented with 10 mM EDTA, beads were incubated in 100 mM Tris-HCl (pH 7.5), 50 mM NaCl, 10 mM EDTA, 100 µg of Proteinase K (Roche), and 0.5% SDS for 30 min at 55° C., from which RNA was recovered by phenol-chloroform extraction. Input RNA was isolated from 1% of the cell lysate using TRIzol after Proteinase K treatment.

In Vitro RNA Pulldown Assay

2 µg of His-YY1 or His-GFP proteins were immobilized with Dynabeads® His-Tag Isolation and Pulldown (Invitrogen) in PBS supplemented with 15 mM β-mercaptoethanol for 2 hrs. 5 µg of total RNA was incubated with protein-bead complexes at room temperature for 1 h in PBS containing 2 mM $MgCl_2$, 0.2 mM $ZnCl_2$, 15 mM β-mercaptoethanol, 100 U/ml RNase Inhibitor, 0.1 mg/ml yeast tRNA (Ambion), 0.05% BSA and 0.2% NP40. RNA was treated with TURBO DNase and renatured by a heat treatment followed by slow cooling down before incubation. Beads were washed with the same incubation buffer supplemented with additional 150 mM NaCl (total 300 mM NaCl). For mutant RNA pulldowns, total RNA was isolated from dox-induced transgenic male MEF lines and less RNA was used (500 ng) because Xist was overexpressed. For RNA fragment pulldowns, each fragment was transcribed in vitro using the MEGAscript® Kit (Ambion). Transcripts were treated with DNase for 1 hr at 37° C., TRIzol-purified, and renatured by heating and slow cooling down. 0.5 pmol of RNA and 1 µg of protein were used per reaction, and 10% of each pulled-down product was analyzed by qRT-PCR. Standard curves for all amplified regions were generated from the same Xist-containing plasmid.

Results

Squelching of Endogenous Xist RNA by Newly Introduced Xist Transgenes

Figure 1B:
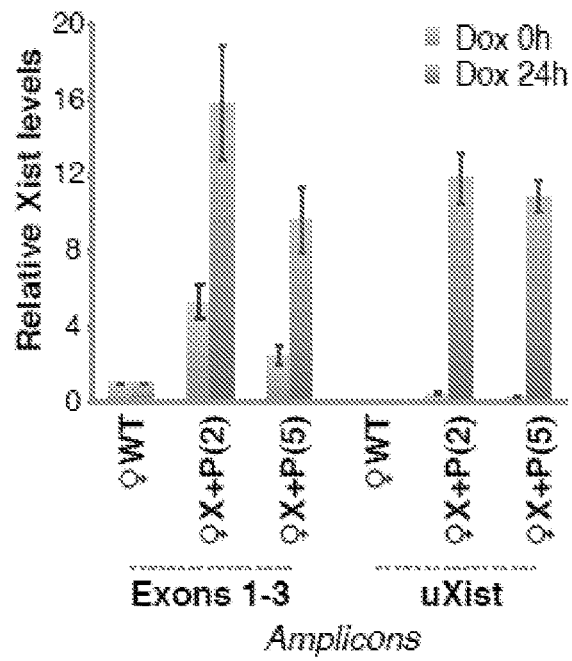
Figure 1C:
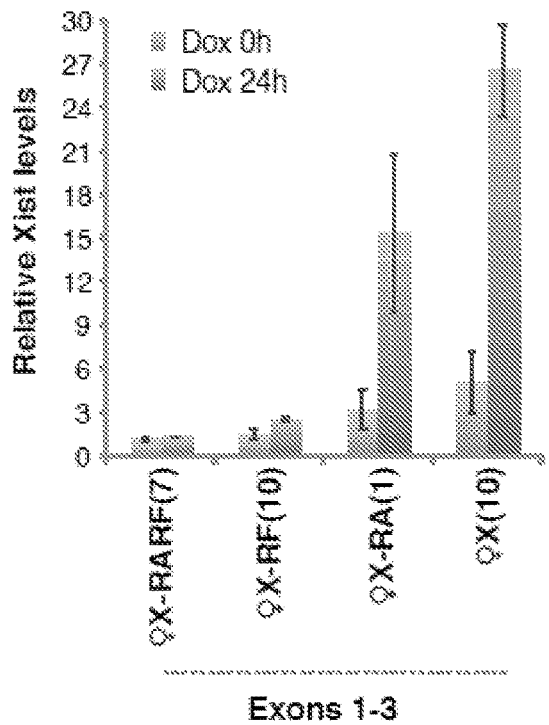

To study Xist RNA localization, a full-length doxycycline (dox)-inducible Xist transgene (X+P; FIG. 1A) was introduced into female mouse embryonic fibroblasts (MEF). RNA fluorescent in situ hybridization (FISH) showed transgene expression and formation of small Xist foci even without dox-induction, likely due to inclusion of 180-bp of Xist's promoter sequence (Pillet et al., 1995; Stavropoulos et al., 2005). [Note: Cells are tetraploid due to SV40 Large T-transformation; two Xi are present]. Dox-induction for 24 hours significantly boosted expression and led to development of large Xist clouds. Quantitative RT-PCR (qRT-PCR) indicated that total Xist levels were 2-5 times higher than in wildtype (WT) cells before dox-induction, and increased 2-3 times further upon induction (FIG. 1C; exons 1-3). To examine transgenic contributions, amplification with transgene-specific primers (uXist) was performed, and >10-fold induction with dox was observed.

Two unusual observations were made. First, the transgene not only formed Xist clouds but was also hypermethylated at H3K27 (H3K27me3) (FIG. 1B). This was unexpected, because previous analyses using a mouse embryonic stem (ES) model showed that the X-chromosome becomes refractory to Xist after the first 3 days of cell differentiation (Wutz and Jaenisch, 2000; Kohlmaier et al., 2004). More surprisingly, ectopic Xist clouds were always more prominent than endogenous clouds. In fact, even before dox induction, the transgene displayed a large Xist cloud and the Xi's RNA cloud was already suppressed in 56-85% of cells (FIG. 1B). After induction, Xist clouds disappeared from Xi completely in 94-98% of cells (FIG. 1B). Multiple independent clones showed this behavior. Thus, newly introduced Xist transgenes in MEFs act on the endogenous locus in trans and "squelches" Xist RNA clouds on Xi.

Squelching Depends on a 700-Bp RNA Localization Domain Around Repeat F

Figure 1D:
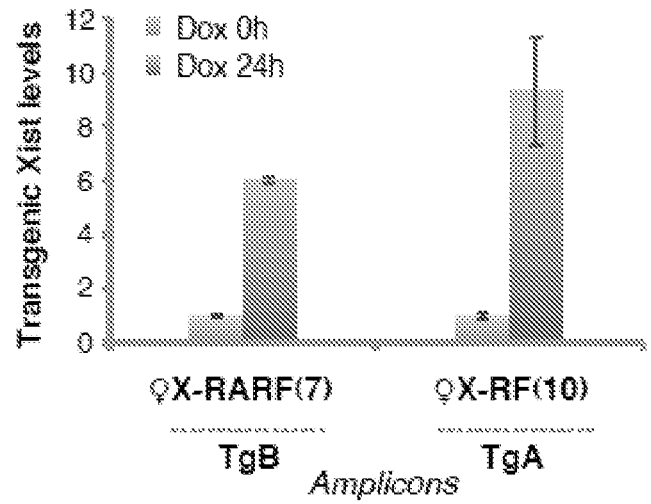

Several mechanisms could underlie squelching. Introduction of homologous transgene sequences could induce RNAi-based transcriptional gene silencing (TGS) (Wassenegger et al., 1994). Alternatively, the transgene could outcompete endogenous Xist for a limited supply of locus-specific transcription factors (Gill and Ptashne, 1988). Post-transcriptional mechanisms, such as those affecting RNA localization, must also be entertained. To address potential mechanisms, transgene deletional analysis was performed to identify squelching sequences. Deletions focused on Xist's conserved proximal end and deleted a 2-kb region spanning Xist's P1 and P2 promoters (Johnston et al., 1998), Repeat A, and Repeat F (Brockdorff et al., 1992; Brown et al., 1992; Nesterova et al., 2001)(FIG. 1A, X-RARF). In contrast to X+P clones, multiple independent clones of X-RARF did not squelch endogenous Xist (FIG. 1C). qRT-PCR showed increased X-RARF expression after dox induction (FIG. 1D), but RNA FISH revealed no RNA accumulation at the X-RARF site. These results implied either an RNA localization or stabilization defect in X-RARF. Thus, the deleted 2-kb region is responsible for both squelching and RNA accumulation.

To narrow down required regions, smaller deletions were made and multiple independent clones of each were examined (representative clones shown in all analyses below). Transgene X deleted only the Xist promoter but had no measurable trans effects (FIG. 1A. The X-RA transgene eliminated the Xist promoter, Repeat A, and RepA RNA (Zhao et al., 2010)(FIG. 1A), but also did not affect squelching or accumulation of Xist transcripts at the transgene site. By contrast, transgene X-RF deleted a 700-bp region around Repeat F and abolished both squelching and RNA localization. Like X-RARF, X-RF induction increased steady state Xist levels (FIG. 1D), but Xist RNA failed to accumulate at the transgene site. At the same time, Xist clouds on Xi were spared. There is thus a strong correlation between transgenic Xist accumulation and squelching of endogenous Xist RNA. Thus, Xist's promoter, Repeat A, and RepA RNA are not required for squelching and implicate the 700-bp region around Repeat F in both Xist localization and squelching.

Xist RNA Diffuses Away from Xi and is Attracted to the Transgene

Figure 1E:
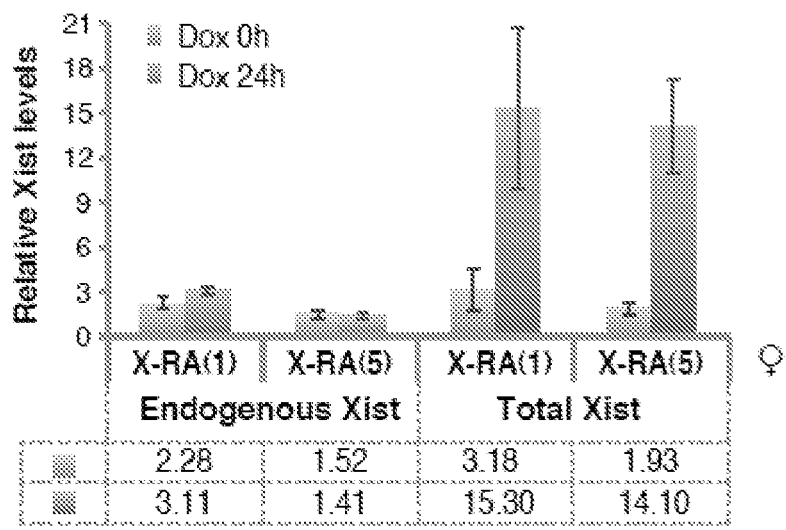

These findings led to suspicion of a direct connection between squelching and RNA localization, as squelching of endogenous Xist occurs when newly introduced Xist transgenes can accumulate RNA. The question was asked whether the transgene could exert trans effects and cause displacement of Xist RNA from Xi. Indeed, although Xist clouds faded away on Xi during squelching, the stability (or steady state levels) of endogenous Xist RNA was surprisingly not affected (FIG. 1E). To investigate the fate of endogenous Xist RNA, Xist molecules were tracked in squelching-competent X-RA clones. Serial RNA/DNA FISH distinguished endogenous versus transgenic RNAs by a Repeat-A probe (FIG. 2A, RA), and X versus transgenic DNA by a vector-specific probe. Intriguingly, endogenous Xist localized not only to Xi but also to the transgenic site. Thus, endogenous Xist RNA trans-migrated between Xi and the homologous ectopic site. This behavior was seen even before dox-induction, demonstrating that high transgene expression is not required to attract Xist RNA away from Xi. H3K27me3 enrichment followed Xist accumulation at the transgene site. Because X-RA lacks Polycomb-recruiting sequences (Zhao et al., 2008), that transgenic H3K27me3 likely reflected the action of wildtype Xist-Polycomb complexes relocalized to the transgene site from Xi. These data show that Xist RNA is diffusible in the nucleus and remains stable when not bound to chromatin.

Because earlier experiments in male cells had shown that transgenic Xist could not diffuse between X and autosome (Lee et al., 1996; Lee et al., 1999; Wutz and Jaenisch, 2000; Kohlmaier et al., 2004), the consequences of introducing these transgenes into male MEFs were examined. Consistent with prior reports, RNA/DNA FISH showed that X-RA male cells formed Xist clouds at the transgene site, but the RNA never transmigrated to the X. Also consistent with previous studies (Plath et al., 2003; Kohlmaier et al., 2004), the Repeat-A-deficient RNA induced H3K27me3 poorly on the autosome in spite of RNA accumulation (H3K27me3 pinpoints were seen at some insertion sites). However, X+P cells efficiently formed Xist clouds and H3K27me3 foci, further arguing that Xist function is not confined to an early developmental time window. Nevertheless, Xist produced from X+P could not bind the male Xa. These results demonstrate that, although diffusible, Xist RNA is not promiscuous. The male Xa is resistant to Xist, either because it lacks a receptor for Xist RNA or other accessory factors.

Xist Localization Requires YY1 Protein

To identify candidate receptors for Xist particles, a "squelching assay" was designed on the principle that RNA binding sites on Xi and transgene must compete for a limited pool of Xist particles. To confirm that the receptors are contained in Xist exon 1, it was asked if Xist exon 1 were sufficient to attract RNA in trans. Transgene X+PE1 (FIG. 2A) was tested in female MEFs by performing RNA FISH using differentially labeled exon 1 and 7 probes that distinguished endogenous from transgenic transcripts. Indeed, exon 1 attracted endogenous Xist RNA, though not as efficiently as full-length transgenes (22% of cells). As observed in other transgenic lines, Xist RNA remained stable when displaced from Xi in X+PE1 cells (FIG. 2B). Combined, these results show that sequences within exon 1 are not only necessary but also sufficient to squelch endogenous Xist. Receptors for Xist particles must therefore reside therein.

Figure 3A:
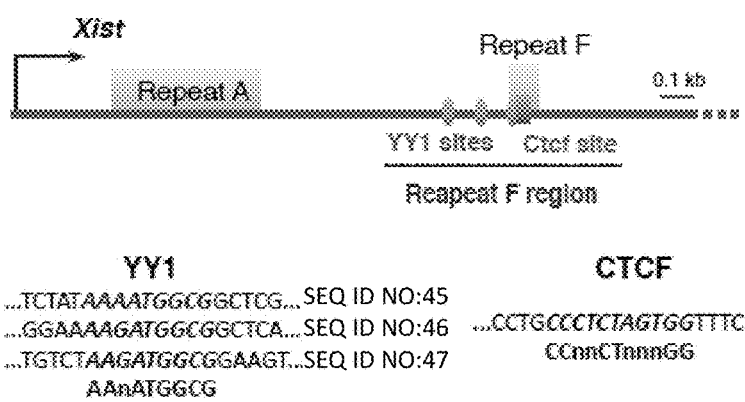
Figure 3B:
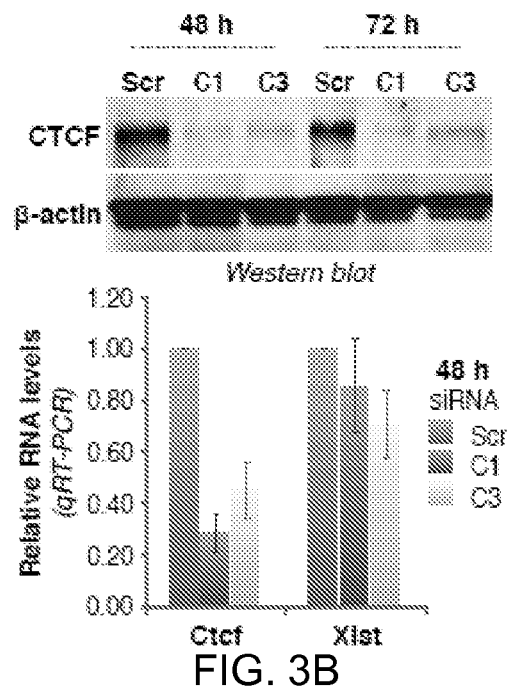
Figure 3C:
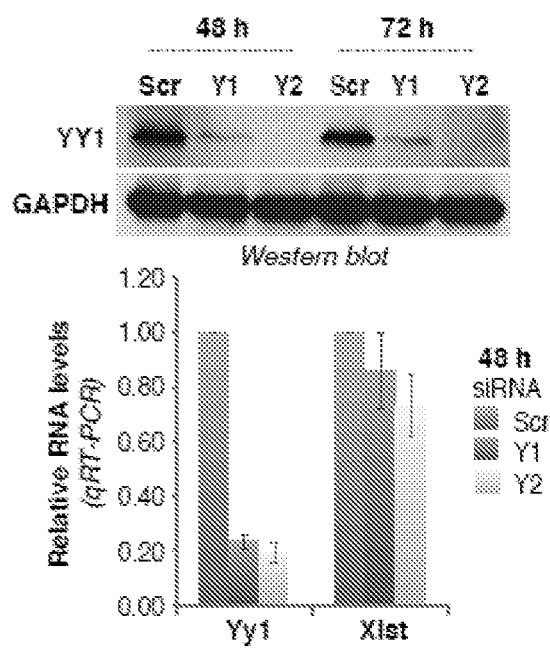

Towards pinpointing specific receptors, exon 1 was searched for conserved motifs. Near Repeat F are two potential binding sites for CTCF (Lobanenkov et al., 1990; Essien et al., 2009) and YY1 (Hariharan et al., 1991; Park and Atchison, 1991; Seto et al., 1991; Shi et al., 1991; Flanagan et al., 1992; Kim et al., 2007)(FIG. 3A). These two proteins have been implicated in other contexts, such as regulation of X-chromosome pairing through binding sites in Tsix/Xite (Donohoe et al., 2007; Xu et al., 2007; Donohoe et al., 2009) and regulation of human XCI through sites upstream of MST (Hendrich et al., 1993; Pugacheva et al., 2005). A role in RNA localization had not been suspected previously. To test whether CTCF is required for Xist localization, good knockdown of CTCF was achieved in female MEFs, but no reduction in Xist levels or clouds was observed (FIG. 3B). Therefore, CTCF is not needed for Xist binding to Xi.

Figure 3D:
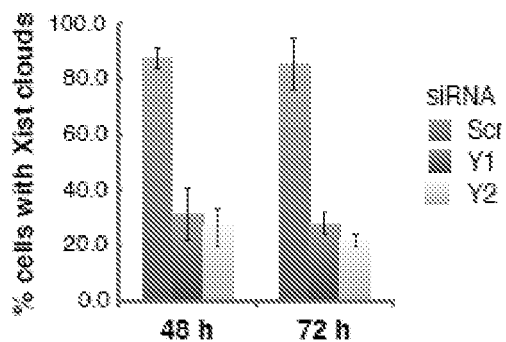
Figure 3E:
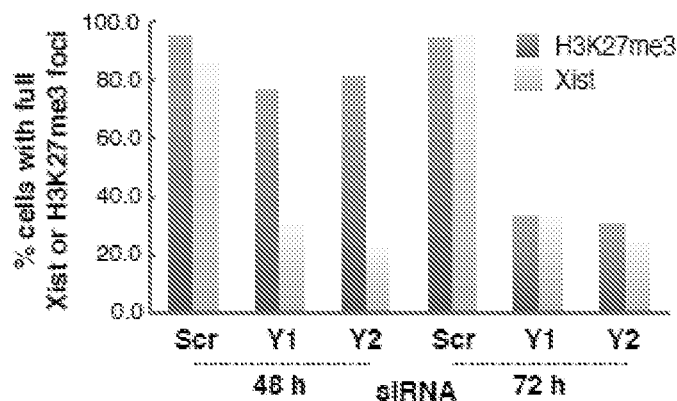

By contrast, knocking down YY1 (FIG. 3C) resulted in loss of Xist clouds from >70% of cells (FIG. 3D). In cells where Xist was still detectable, RNA signals were pinpoint or severely attenuated (arrows, FIG. 3D). Similar results were obtained for two YY1-specific siRNAs, Y1 and Y2, arguing against off-target effects. Transfection with scrambled siRNA (siRNA-Scr) had no effect on YY1 or Xist. Interestingly, although YY1 knockdown affected Xist localization, it did not affect total RNA levels, agreeing with conclusions drawn from the transgene studies that Xist RNA remains stable when displaced from chromatin. Whereas Xist clouds disappeared within 24-48 h of YY1 knockdown, H3K27me3 enrichment persisted up to 48 h and did not disappear from Xi until 72 h (FIG. 3E; 70-80%), consistent with slower kinetics of H3K27me3 turnover. These data demonstrate that YY1 is essential for Xist localization.

A Trio of YY1-Binding Sites Serves as Nucleation Center

The data implicate YY1 as a potential receptor for Xist particles. To investigate this idea, three conserved elements matching the YY1 consensus, AAnATGGCG, separated by ~100 bp near Repeat F were examined. These elements were previously proposed to bind YY1 based on bioinformatic and ChIP analyses, though direct DNA-protein interactions were not demonstrated (Kim et al., 2007). To test direct binding, electrophoretic mobility shift assays (EMSA) were performed and purified recombinant YY1 protein shifted a 280-bp DNA probe containing the trio motif (FIG. 4A,B). Elevating YY1 protein concentration both intensified the shifted band (arrow) and led to appearance of two higher molecular weight species (asterisks) indicative of progressive site occupancy. When the motifs were mutated, YY1 binding was severely attenuated (FIG. 4A,B). Thus, YY1 directly binds the trio motif.

To ask if the trio motif is involved in Xist localization, site-directed mutagenesis was performed at all three YY1 sites on the X-RA transgene (X-RA$^{Yy1m}$; FIG. 4A). X-RA was used because it is both squelching-competent and its RNA can be distinguished from endogenous Xist RNA by RNA FISH using a Repeat A probe. Serial RNA/DNA FISH showed dramatic differences between X-RA and X-RA$^{Yy1m}$ clones. Before dox induction, RNA was never observed at the X-RA$^{Yy1m}$ transgenic site, whereas Xist RNA showed robust accumulation on Xi. This result contrasted with obvious squelching in uninduced X-RA clones. Dox induction revealed further differences. Transgene expression resulted in a huge burst of RNA around the transgene site, but the RNA seemed to diffuse away rather than localize (a concentration gradient was seen around the transgene; 62.9%, n=116). Thus, mutating the YY1-binding sites prevented anchoring of Xist RNA and abolished the transgene's ability to squelch Xist RNA from Xi. In wildtype cells, YY1 protein did not decorate Xi at any time. Thus, a trio of YY1-binding sites serves as nucleation center for Xist binding to Xi.

Xist Diffuses Bidirectionally Between Xi and Transgene, but Xa is Always Resistant Curiously, two Xi in transgenic cells often did not have equal Xist clouds. The Xi closer to the transgene usually exhibited the larger Xist cloud (49.1%, n=116) and, strangely, this cloud consisted mostly of mutated transgenic rather than Xi-synthesized RNA, as RA-probe signals on proximal Xi were less than on distal Xi. This disparity was observed only after dox-induction. Therefore, transgenic RNA—though it could not bind to its own transgene site in cis—must be able to displace endogenous Xist from the Xi closer to it. This odd finding implied that YY1 must interact with DNA and RNA via different nucleic acid motifs. qRT-PCR showed no change in steady state levels of endogenous or transgenic RNA (FIG. 4C), indicating that mutated as well as wildtype Xist molecules are likely stable even when not chromatin-bound.

At no time did transgenic Xist localize onto Xa, even when Xa was in proximity in female cells. This was also the case in male MEF clones carrying X-RA$^{Yy1m}$. Prior to dox induction, transgene expression was minimal. Pinpoint nascent Xist transcripts were seen in 68% of cells (n=78), and the rest showed no detectable Xist. When induced, transgenic RNA localized poorly around the transgene site (81%, n=74), similar to that observed in X-RA$^{Yy1m}$ female cells. In males, Xa never attracted Xist RNA even when the transgene locus was close. Xa is therefore always resistant.

Taken together, these data illustrate several crucial points: (i) A cluster of YY1 sites near Repeat F serves nucleation center for Xist binding. (ii) Xist particles are freely diffusible. (iii) Exchange of Xist molecules can occur bidirectionally, from transgene to Xi (FIG. 4C) as well as from Xi to transgene (FIGS. 1-2). (iv) While X-RA$^{Yy1m}$ transgenes could not strip Xist RNA from Xi, Xi could attract RNA produced by X-RA$^{Yy1m}$. This lack of reciprocity argues that, while YY1 binds the AAnATGGCG motif in DNA, its interaction with Xist RNA does not occur through the corresponding RNA motif, AAnAUGGCG. (v) Xa is refractory to Xist binding, even though Xa also possesses the trio of YY1 sites.

Xi-Specific Binding of YY1

Xa's immunity implies an epigenetic difference between Xa from Xi. To ask if differential YY1 binding could underlie the difference, YY1 binding patterns were examined in vivo by chromatin immunoprecipitation (ChIP) assays using YY1 antibodies and qPCR primers flanking the YY1 sites (FIG. 5A). Strong enrichment of YY1 to this region (uRF) was observed in female but not male MEFs (FIG. 5B). The enrichment was comparable to that for intron 1 of Peg3, an imprinted gene known to bind YY1 (Kim et al., 2009). By contrast, no enrichment occurred in a region downstream of the Repeat C (dRC) or in the H19 imprinting control center (ICR). These data demonstrate that YY1 specifically occupies the Repeat F YY1 sites. To distinguish Xa from Xi, female MEFs were used that bear a conditional deletion of Xist exons 1-3 either on Xa (XiXa$^{\Delta Xist}$) or Xi (XaXi$^{\Delta Xist}$)(Zhang et al., 2007). ChIP consistently showed enriched YY1 binding to uRF in XiXa$^{\Delta Xist}$ but not in XaXi$^{\Delta Xist}$. In XiXa$^{\Delta Xist}$, YY1 could only have bound to Xi, as the uRF region is deleted on Xa. By the same logic, the lack of YY1 enrichment at uRF in XaXi$^{\Delta Xist}$ cells implies that YY1 is not enriched on Xa. Thus, YY1 differentially binds the nucleation center of Xi and Xa. Thus differential susceptibility of Xa and Xi to Xist is likely not only the result of allele-specific Xist transcription, but primarily the consequence of allele-specific YY1 occupancy. In differentiating female ES cells, knockdown of YY1 also did not alter the stability of Xist RNA but significantly interfered with Xist localization (FIG. 5C). Therefore, YY1 is likely crucial for Xist localization throughout the XCI process (initiation, establishment, and maintenance).

YY1 is an RNA-binding protein and serves as receptor for Xist

If YY1 serves as docking protein for Xist silencing complexes, it must directly interact with Xist RNA. To look for interactions in vivo, RNA immunoprecipitation (RIP) was performed with YY1 antibodies following UV-crosslinking of RNA to protein in MEFs. qRT-PCR of YY1 pulldown material showed significant co-immunoprecipitation of Xist RNA (FIG. 6A,B). The interaction was not detected without UV crosslinking, in RT-negative samples, and when IgG antibodies were used. Moreover, the abundant U1 snRNA was not co-immunoprecipitated. Because UV crosslinking occurs at near-zero Angstrom, the observed pulldown suggests specific and direct Xist-YY1 interaction in vivo.

To probe its nature, out RNA pulldown assays were carried in vitro using purified recombinant His-tagged YY1 proteins. To ask if YY1 preferentially binds Xist RNA among a complex pool of cellular RNAs, total RNA was purified from female MEFs and quantitated the interaction between YY1 and Xist relative to other RNAs. At multiple qPCR positions (uRF, uRA, dRE), Xist pulldown by YY1 was enriched above background (GFP)(FIG. 6C). Neither Gapdh nor a-tubulin RNA showed enrichment. Therefore, consistent with in vivo RIP, YY1 specifically and directly interacts with Xist in vitro.

Site-directed mutagenesis showed that, although YY1 binds exon 1 DNA via the motif, AAnATGGCG, YY1 cannot bind Xist RNA via the corresponding motif in the RNA (AAnAUGGCG) (FIG. 4). To determine where YY1 binds RNA, pulldown assays were carried out using a panel of mutated transgenic RNAs (FIG. 6A). To isolate transgenic RNAs from endogenous Xist, the transgenic constructs were introduced into male MEFs, induced expression using doxycycline, isolated RNA, and tested the RNA for binding to YY1 in a pulldown assay. All four transgenic RNAs bound YY1 specifically (FIG. 6D, P<0.02 in all cases). The control Gapdh RNA did not demonstrate significant differences between pulldown with YY1 versus GFP. These results show that deleting Repeat A (X-RA) and mutating the clustered YY1 motifs (X-RA$^{YY1m}$) had no effect on Xist-YY1 interactions, further supporting the notion that YY1 does not bind Xist via AAnAUGGCG.

The ability of X-RAE1 RNA to bind YY1 delimits the interaction domain to the portion of exon 1 downstream of Repeat A (FIG. 6A). To pinpoint Xist RNA's YY1-binding domain, RNA subfragments were generated, in vitro-transcribed and purified each, and tested them for YY1 binding in a pulldown assay (FIG. 6E). Although several RNA domains showed more binding to YY1 than background (GFP), the difference was strongest and statistically significant only for fragments containing Repeat C, a conserved C-rich element unique to Xist that is repeated 14 times in tandem (Brockdorff et al., 1992; Brown et al., 1992). Repeat C by itself showed 20-fold enrichment (P=0.047). A fragment containing both Repeats B and C showed 10-fold better binding than background (P=0.033). Repeat B might also have some affinity for YY1, as it showed 5-fold enrichment and the difference bordered statistical significance (P=0.053). Repeat C's binding to YY1 was especially interesting, given recent observation that locked nucleic acid (LNA) antagomirs against this repeat displace Xist RNA from Xi without affecting RNA stability (Sarma et al., 2010)—a finding that suggested Repeat C as an anchoring sequence to Xi. Thus Repeat C, and potentially also Repeat B, of Xist RNA likely make direct contact with YY1, which in turn anchors the Xist particle to Xi via a trio of DNA elements near Repeat F (FIG. 6F). Thus, YY1 is an RNA-binding protein that serves as receptor for the Xist silencing complex on Xi.

Example 2. Preparation of a Library of YY1-Interacting lncRNAs Using RIP-Seq

A library of YY1-interacting lncRNAs is prepared using RIP-Seq or CLIP-seq.

RIP-Seq Library

RNA immunoprecipitation is performed (Zhao et al., 2008) using $10^7$ wildtype 16.7 (Lee and Lu, 1999) and Ezh2−/− (Shen et al., 2008) ES cells. To construct RIP-seq libraries, cell nuclei are isolated, nuclear lysates were prepared, treated with 400 U/ml DNAse, and incubated with anti-YY1 antibodies (Active Motif) or control IgG (Cell Signaling Technology). RNA-protein complexes are immunoprecipitated with protein A agarose beads and RNA extracted using Trizol (Invitrogen). To preserve strand information, template switching is used for the library construction (Cloonan et al., 2008). 20-150 ng RNA and Adaptor1 (5'-CTTTCCCTACACGACGCTCT TCCGATCT-3') are used for first-strand cDNA synthesis using Superscript II Reverse Transcription Kit (Invitrogen). Superscript II adds non-template CCC 3' overhangs, which were used to hybridize to Adaptor2-GGG template-switch primer (5'-CAAGCAGAAGACGGCATACGAGCTCTTC-CGATCTGGG-3'). During 1$^{st}$-strand cDNA synthesis, samples are incubated with adaptor1 at 20° C. for 10 min, followed by 37° C. for 10 min and 42° C. for 45 min. Denatured template switch primer is then added and each tube incubated for 30 min at 42° C., followed by 75° C. for 15 min. Resulting cDNAs are amplified by forward (5'-AATGATACGGCGACCACCGAGATCTACA CTCTTTC-CCTACACGACGCTCTTCCGATCT-3') and reverse (5'-CAAGCAGAAGACGGCATACGAGCTCTTCCGATCT-3') Illumina primers. PCR is performed by Phusion polymerase (BioRad) as follows: 98° C. for 30 s, 20-24 cycles of [98° C. 10 s, 65° C. 30 s, 72° C. 30 s], and 72° C.

for 5 min. PCR products are loaded on 3% NuSieve gel for size-selection and 200-1,200 bp products are excised and extracted by QIAEX II Agarose Gel Extraction Kit (Qiagen). Minus-RT samples are expected to yield no products. DNA concentrations are quantitated by PicoGreen. 5-10 ml of 2-20 nM cDNA samples are sequenced.

CLIP-Seq Library

A CLIP-Seq library is prepared as described above for the RIP-Seq library, with the additional steps of UV crosslinking before the IP Seq is performed, a limited RNAse step to reduce the fragment size of interacting RNAs, electroporesis of IP material in an SDS-PAGE gel, and excision of specific RNA-protein bands. CLIP-seq libraries will be made from nuclear lysates and/or the chromatin fraction. Exemplary methods for performing CLIP-Seq are described at Yeo et al., Nat Struct Mol Biol. 2009 February; 16(2):130-7. Epub 2009 Jan. 11; Zhang and Darnell, "Mapping in vivo protein-RNA interactions at single-nucleotide resolution from HITS-CLIP data." Nat Biotechnol. 2011 Jun. 1; Jensen and Darnell, Methods Mol Biol. 2008; 488:85-98; Licatalosi et al., Nature. 2008 Nov. 27; 456(7221):464-9. Epub 2008 Nov. 2; Ule et al., Methods. 2005 December; 37(4):376-86; and Ule et al., Science. 2003 Nov. 14; 302(5648):1212-5.

Bioinformatic Analysis

Except as noted below, all analyses are performed using custom C++ programs. Image processing and base calling were performed using the Illumina pipeline. 3' adaptor sequences were detected by crossmatch and matches of bases are trimmed, homopolymer reads filtered, and reads matching the mitochondrial genome and ribosomal RNAs excluded from all subsequent analyses. Remaining sequences are then aligned to the reference genome using shortQueryLookup (Batzoglou et al., 2002). Alignments with ≤1 error are retained. Because library construction and sequencing generate sequence from the opposite strand of the YY1-bound RNA, in all further analysis, each read is treated as if it were reverse-complemented. To determine the correlation coefficients comparing the original a-YY1 RIP-seq library to its technical and biological replicates and also to RIP-seq of the YY1$^{-/-}$ control line, the number of reads per gene between two samples is compared and, for each pair, the Pearson correlation between the number of reads mapped to each refGene is computed. That is, for each sample, a vector of counts of reads mapped to each refGene is created and the Pearson correlation between all pairs of vectors is computed.

Locations of repetitive sequences in the reference genome (RepeatMasker) are obtained from the UCSC Genome Browser database (Kent et al., The human genome browser at UCSC. Genome Res. 2002 June; 12(6):996-1006; Fujita et al., "The UCSC Genome Browser database: update 2011." Nucleic Acids Res. 2010 Oct. 18) The overlap of YY1 transcriptome reads with these repeats is obtained by intersecting coordinates of RepeatMasker data with coordinates of read alignments. The UCSC transcriptome was used as general reference (available online at hgdownload.cse.ucsc.edu/goldenPath/mm9/database/transcriptome.txt.gz). To obtain a set of non-overlapping distinct transcribed regions, the UCSC transcriptome transcripts are sorted by start coordinate and merged overlapping transcripts on the same strand (joined UCSC transcriptome: 39,003 transcripts total). Read alignment coordinates are then intersected with those of the merged UCSC transcripts to determine the number of UCSC transcripts present in the PRC2 transcriptome. Hits to the transcripts are converted to RPKM units, where the read count is $1/(n*K*M)$, and n is the number of alignments in the genome, K is the transcript length divided by 1,000, and M is the sequencing depth including only reads mapping to mm9 divided by 1,000,000 (Mortazavi et al., 2008). This normalization allows for comparisons between transcripts of differing lengths and between samples of differing sequencing depths. To generate promoter maps, promoter regions are defined as −10,000 to +2000 bases relative to TSS (obtained from refGene catalog, UCSC Genome Browser). Read counts overlapping promoter regions are plotted, except that the limit of 10 alignments was relaxed. For chromosomal alignments, read numbers are computed for all non-overlapping consecutive 100 kb windows on each chromosome. Reads are normalized such that those mapping to n locations are counted as $1/n^{th}$ of a read at each location. A list of all enriched transcripts is found by comparing the RPKM scores on each strand for all transcripts in the WT and YY1$^{-/-}$ samples. Then their coordinates are intersected with coordinates of the feature of interest.

REFERENCES

Atchison, L., Ghias, A., Wilkinson, F., Bonini, N., and Atchison, M. L. (2003). Transcription factor YY1 functions as a PcG protein in vivo. EMBO J 22, 1347-1358

Brockdorff, N., Ashworth, A., Kay, G. F., McCabe, V. M., Norris, D. P., Cooper, P. J., Swift, S., and Rastan, S. (1992). The product of the mouse Xist gene is a 15 kb inactive X-specific transcript containing no conserved ORF and located in the nucleus. Cell 71, 515-526

Brown, C. J., Hendrich, B. D., Rupert, J. L., Lafreniere, R. G., Xing, Y., Lawrence, J., and Willard, H. F. (1992). The human XIST gene: analysis of a 17 kb inactive X-specific RNA that contains conserved repeats and is highly localized within the nucleus. Cell 71, 527-542

Brown, C. J., Lafreniere, R. G., Powers, V. E., Sebastio, G., Ballabio, A., Pettigrew, A. L., Ledbetter, D. H., Levy, E., Craig, I. W., and Willard, H. F. (1991). Localization of the X inactivation centre on the human X chromosome in Xq13. Nature 349, 82-84

Chow, J. C., Hall, L. L., Baldry, S. E., Thorogood, N. P., Lawrence, J. B., and Brown, C. J. (2007). Inducible XIST-dependent X-chromosome inactivation in human somatic cells is reversible. Proc Natl Acad Sci USA 104, 10104-10109

Clemson, C. M., Chow, J. C., Brown, C. J., and Lawrence, J. B. (1998). Stabilization and localization of Xist RNA are controlled by separate mechanisms and are not sufficient for X inactivation. J Cell Biol 142, 13-23

Clemson, C. M., McNeil, J. A., Willard, H. F., and Lawrence, J. B. (1996). XIST RNA paints the inactive X chromosome at interphase: evidence for a novel RNA involved in nuclear/chromosome structure. J Cell Biol 132, 259-275

Csankovszki, G., Panning, B., Bates, B., Pehrson, J. R., and Jaenisch, R. (1999). Conditional deletion of Xist disrupts histone macroH2A localization but not maintenance of X inactivation. Nat Genet 22, 323-324

Donohoe, M. E., Silva, S. S., Pinter, S. F., Xu, N., and Lee, J. T. (2009). The pluripotency factor Oct4 interacts with Ctcf and also controls X-chromosome pairing and counting. Nature 460, 128-132

Donohoe, M. E., Zhang, L. F., Xu, N., Shi, Y., and Lee, J. T. (2007). Identification of a Ctcf cofactor, Yy1, for the X chromosome binary switch. Mol Cell 25, 43-56

Essien, K., Vigneau, S., Apreleva, S., Singh, L. N., Bartolomei, M. S., and Hannenhalli, S. (2009). CTCF binding site classes exhibit distinct evolutionary, genomic, epigenomic and transcriptomic features. Genome Biol 10, R131

Flanagan, J. R., Becker, K. G., Ennist, S. L., Gleason, P. H., Driggers, B. Z., Levi, E., Appella, and Ozato, K. (1992). Cloning of a negative transcription factor that binds to the upstream conserved region of Moloney murine leukemia virus. Mol Cell Biol 12, 38-44

Gartler, S. M., and Riggs, A. D. (1983). Mammalian X-chromosome inactivation. Annu Rev Genet 17, 155-190

Gill, G., and Ptashne, M. (1988). Negative effect of the transcriptional activator GAL4. Nature 334, 721-724

Hariharan, N., Kelley, D. E., and Perry, R. P. (1991). Delta, a transcription factor that binds to downstream elements in several polymerase II promoters, is a functionally versatile zinc finger protein. Proc Natl Acad Sci USA 88, 9799-9803

Hendrich, B. D., Brown, C. J., and Willard, H. F. (1993). Evolutionary conservation of possible functional domains of the human and murine XIST genes. Hum Mol Genet 2, 663-672

Hochedlinger, K., Yamada, Y., Beard, C., and Jaenisch, R. (2005). Ectopic expression of Oct-4 blocks progenitor-cell differentiation and causes dysplasia in epithelial tissues. Cell 121, 465-477

Iuchi, S. (2001). Three classes of C2H2 zinc finger proteins. Cell Mol Life Sci 58, 625-635 Johnston, C. M., Nesterova, T. B., Formstone, E. J., Newall, A. E., Duthie, S. M., Sheardown, S. A., and Brockdorff, N. (1998). Developmentally regulated Xist promoter switch mediates initiation of X inactivation. Cell 94, 809-817

Jonkers, I., Monkhorst, K., Rentmeester, E., Grootegoed, J. A., Grosveld, F., and Gribnau, J. (2008). Xist RNA is confined to the nuclear territory of the silenced X chromosome throughout the cell cycle. Mol Cell Biol 28, 5583-5594

Kim, J. D., Hinz, A. K., Choo, J. H., Stubbs, L., and Kim, J. (2007). YY1 as a controlling factor for the Peg3 and Gnas imprinted domains. Genomics 89, 262-269

Kim, J. D., Kang, K., and Kim, J. (2009). YY1's role in DNA methylation of Peg3 and Xist. Nucleic Acids Res 37, 5656-5664

Kohlmaier, A., Savarese, F., Lachner, M., Martens, J., Jenuwein, T., and Wutz, A. (2004). A chromosomal memory triggered by Xist regulates histone methylation in X inactivation. PLoS Biol 2, E171

Ku, M., Koche, R. P., Rheinbay, E., Mendenhall, E. M., Endoh, M., Mikkelsen, T. S., Presser, A., Nusbaum, C., Xie, X., Chi, A. S., et al. (2008). Genomewide analysis of PRC1 and PRC2 occupancy identifies two classes of bivalent domains. PLoS Genet 4, e1000242

Kuzmichev, A., Nishioka, K., Erdjument-Bromage, H., Tempst, P., and Reinberg, D. (2002). Histone methyltransferase activity associated with a human multiprotein complex containing the Enhancer of Zeste protein. Genes Dev 16, 2893-2905

Landeira, D., Sauer, S., Poot, R., Dvorkina, M., Mazzarella, L., Jorgensen, H. F., Pereira, C. F., Leleu, M., Piccolo, F. M., Spivakov, M., et al. (2010). Jarid2 is a PRC2 component in embryonic stem cells required for multi-lineage differentiation and recruitment of PRC1 and RNA Polymerase II to developmental regulators. Nat Cell Biol 12, 618-624

Laverty, C., Lucci, J., and Akhtar, A. (2010). The MSL complex: X chromosome and beyond. Curr Opin Genet Dev 20, 171-178

Lee, J. T. (2000). Disruption of imprinted X inactivation by parent-of-origin effects at Tsix. Cell 103, 17-27

Lee, J. T. (2009). Lessons from X-chromosome inactivation: long ncRNA as guides and tethers to the epigenome. Genes Dev 23, 1831-1842

Lee, J. T. (2010). The X as model for RNA's niche in epigenomic regulation. Cold Spring Harb Perspect Biol 2, a003749

Lee, J. T., and Lu, N. (1999). Targeted mutagenesis of Tsix leads to nonrandom X inactivation. Cell 99, 47-57

Lee, J. T., Lu, N., and Han, Y. (1999). Genetic analysis of the mouse X inactivation center defines an 80-kb multifunction domain. Proc Natl Acad Sci USA 96, 3836-3841

Lee, J. T., Strauss, W. M., Dausman, J. A., and Jaenisch, R. (1996). A 450 kb transgene displays properties of the mammalian X-inactivation center. Cell 86, 83-94

Li, G., Margueron, R., Ku, M., Chambon, P., Bernstein, B. E., and Reinberg, D. (2010). Jarid2 and PRC2, partners in regulating gene expression. Genes Dev 24, 368-380

Lobanenkov, V. V., Nicolas, R. H., Adler, V. V., Paterson, H., Klenova, E. M., Polotskaja, A. V., and Goodwin, G. H. (1990). A novel sequence-specific DNA binding protein which interacts with three regularly spaced direct repeats of the CCCTC-motif in the 5' flaking sequence of the chicken c-myc gene. Oncogene 5, 1743-1753

Lucchesi, J. C., Kelly, W. G., and Panning, B. (2005). Chromatin remodeling in dosage compensation. Annu Rev Genet 39, 615-651

Luikenhuis, S., Wutz, A., and Jaenisch, R. (2001). Antisense transcription through the Xist locus mediates Tsix function in embryonic stem cells. Mol Cell Biol 21, 8512-8520

Lyon, M. F. (1961). Gene action in the X-chromosome of the mouse (*Mus musculus* L.). Nature 190, 372-373

Marahrens, Y., Panning, B., Dausman, J., Strauss, W., and Jaenisch, R. (1997). Xist-deficient mice are defective in dosage compensation but not spermatogenesis. Genes Dev 11, 156-166

Mendenhall, E. M., Koche, R. P., Truong, T., Zhou, V. W., Issac, B., Chi, A. S., Ku, M., and Bernstein, B. E. (2010). GC-rich sequence elements recruit PRC2 in mammalian ES cells. PLoS Genet 6, e1001244

Meyer, B. J. (2010). Targeting X chromosomes for repression. Curr Opin Genet Dev 20, 179-189

Morey, C., Navarro, P., Debrand, E., Avner, P., Rougeulle, C., and Clerc, P. (2004). The region 3' to Xist mediates X chromosome counting and H3 Lys-4 dimethylation within the Xist gene. Embo J 23, 594-604

Nesterova, T. B., Slobodyanyuk, S. Y., Elisaphenko, E. A., Shevchenko, A. I., Johnston, C., Pavlova, M. E., Rogozin, I. B., Kolesnikov, N. N., Brockdorff, N., and Zakian, S. M. (2001). Characterization of the genomic Xist locus in rodents reveals conservation of overall gene structure and tandem repeats but rapid evolution of unique sequence. Genome Res 11, 833-849

Ogawa, Y., and Lee, J. T. (2003). Xite, X-inactivation intergenic transcription elements that regulate the probability of choice. Mol Cell 11, 731-743

Ogawa, Y., Sun, B. K., and Lee, J. T. (2008). Intersection of the RNA interference and X-inactivation pathways. Science 320, 1336-1341

Ohhata, T., Hoki, Y., Sasaki, H., and Sado, T. (2008). Crucial role of antisense transcription across the Xist promoter in Tsix-mediated Xist chromatin modification. Development 135, 227-235

Pal Bhadra, M., Bhadra, U., and Birchler, J. A. (2006). Misregulation of sex-lethal and disruption of male-specific lethal complex localization in *Drosophila* species hybrids. Genetics 174, 1151-1159

Park, K., and Atchison, M. L. (1991). Isolation of a candidate repressor/activator, NF-E1, that binds to the immunoglobulin kappa 3' enhancer and the immunoglobulin heavy-chain mu E1 site. Proc Natl Acad Sci USA 88, 9804-9808

Park, Y., Mengus, G., Bai, X., Kageyama, Y., Meller, V. H., Becker, P. B., and Kuroda, M. I. (2003). Sequence-specific targeting of *Drosophila* roX genes by the MSL dosage compensation complex. Mol Cell 11, 977-986

Payer, B., and Lee, J. T. (2008). X Chromosome Dosage Compensation: How Mammals Keep the Balance. Annu Rev Genet 42, 733-772

Penny, G. D., Kay, G. F., Sheardown, S. A., Rastan, S., and Brockdorff, N. (1996). Requirement for Xist in X chromosome inactivation. Nature 379, 131-137

Pillet, N., Bonny, C., and Schorderet, D. F. (1995). Characterization of the promoter region of the mouse Xist gene. Proc Natl Acad Sci USA 92, 12515-12519

Plath, K., Fang, J., Mlynarczyk-Evans, S. K., Cao, R., Worringer, K. A., Wang, H., de la Cruz, C. C., Otte, A. P., Panning, B., and Zhang, Y. (2003). Role of histone H3 lysine 27 methylation in X inactivation. Science 300, 131-135

Pugacheva, E. M., Tiwari, V. K., Abdullaev, Z., Vostrov, A. A., Flanagan, P. T., Quitschke, W. W., Loukinov, D. I., Ohlsson, R., and Lobanenkov, V. V. (2005). Familial cases of point mutations in the XIST promoter reveal a correlation between CTCF binding and pre-emptive choices of X chromosome inactivation. Hum Mol Genet 14, 953-965

Ringrose, L., and Paro, R. (2004). Epigenetic regulation of cellular memory by the Polycomb and Trithorax group proteins. Annu Rev Genet 38, 413-443

Sado, T., Wang, Z., Sasaki, H., and Li, E. (2001). Regulation of imprinted X-chromosome inactivation in mice by Tsix. Development 128, 1275-1286

Sarma, K., Levasseur, P., Aristarkhov, A., and Lee, J. T. (2010). Locked nucleic acids reveal sequence requirements and kinetics of Xist RNA localization to the X chromosome. Proc Natl Acad Sci USA in press Schoeftner, S., Sengupta, A. K., Kubicek, S., Mechtler, K., Spahn, L., Koseki, H., Jenuwein, T., and Wutz, A. (2006). Recruitment of PRC1 function at the initiation of X inactivation independent of PRC2 and silencing. Embo J 25, 3110-3122

Schwartz, Y. B., and Pirrotta, V. (2008). Polycomb complexes and epigenetic states. Curr Opin Cell Biol 20, 266-273

Seto, E., Shi, Y., and Shenk, T. (1991). YY1 is an initiator sequence-binding protein that directs and activates transcription in vitro. Nature 354, 241-245

Shi, Y., Seto, E., Chang, L. S., and Shenk, T. (1991). Transcriptional repression by YY1, a human GLI-Kruppel-related protein, and relief of repression by adenovirus E1A protein. Cell 67, 377-388

Silva, J., Mak, W., Zvetkova, I., Appanah, R., Nesterova, T. B., Webster, Z., Peters, A. H., Jenuwein, T., Otte, A. P., and Brockdorff, N. (2003). Establishment of histone h3 methylation on the inactive X chromosome requires transient recruitment of Eed-Enx1 polycomb group complexes. Dev Cell 4, 481-495

Starmer, J., and Magnuson, T. (2009). A new model for random X chromosome inactivation. Development 136, 1-10

Stavropoulos, N., Lu, N., and Lee, J. T. (2001). A functional role for Tsix transcription in blocking Xist RNA accumulation but not in X-chromosome choice. Proc Natl Acad Sci USA 98, 10232-10237

Stavropoulos, N., Rowntree, R. K., and Lee, J. T. (2005). Identification of developmentally specific enhancers for Tsix in the regulation of X chromosome inactivation. Mol Cell Biol 25, 2757-2769

Sun, B. K., Deaton, A. M., and Lee, J. T. (2006). A transient heterochromatic state in Xist preempts X inactivation choice without RNA stabilization. Mol Cell 21, 617-628

Takahashi, Y., Rayman, J. B., and Dynlacht, B. D. (2000). Analysis of promoter binding by the E2F and pRB families in vivo: distinct E2F proteins mediate activation and repression. Genes Dev 14, 804-816

Tian, D., Sun, S., and Lee, J. T. (2010). The long noncoding RNA, Jpx, is a molecular switch for X chromosome inactivation. Cell 143, 390-403

Vigneau, S., Augui, S., Navarro, P., Avner, P., and Clerc, P. (2006). An essential role for the DXPas34 tandem repeat and Tsix transcription in the counting process of X chromosome inactivation. Proc Natl Acad Sci USA 103, 7390-7395

Wassenegger, M., Heimes, S., Riedel, L., and Sanger, H. L. (1994). RNA-directed de novo methylation of genomic sequences in plants. Cell 76, 567-576

Wilkinson, F. H., Park, K., and Atchison, M. L. (2006). Polycomb recruitment to DNA in vivo by the YY1 REPO domain. Proc Natl Acad Sci USA 103, 19296-19301

Woo, C. J., Kharchenko, P. V., Daheron, L., Park, P. J., and Kingston, R. E. (2010). A region of the human HOXD cluster that confers Polycomb-group responsiveness. Cell 140, 99-110

Wutz, A., and Gribnau, J. (2007). X inactivation Xplained. Curr Opin Genet Dev 17, 387-393

Wutz, A., and Jaenisch, R. (2000). A shift from reversible to irreversible X inactivation is triggered during ES cell differentiation. Mol Cell 5, 695-705

Wutz, A., Rasmussen, T. P., and Jaenisch, R. (2002). Chromosomal silencing and localization are mediated by different domains of Xist RNA. Nat Genet 30, 167-174

Xu, N., Donohoe, M. E., Silva, S. S., and Lee, J. T. (2007). Evidence that homologous X-chromosome pairing requires transcription and Ctcf protein. Nat Genet 39, 1390-1396

Zhang, L. F., Huynh, K. D., and Lee, J. T. (2007). Perinucleolar targeting of the inactive X during S phase: evidence for a role in the maintenance of silencing. Cell 129, 693-706

Zhao, J., Ohsumi, T. K., Kung, J. T., Ogawa, Y., Grau, D. J., Sarma, K., Song, J. J., Kingston, R. E., Borowsky, M., and Lee, J. T. (2010). Genome-wide identification of polycomb-associated RNAs by RIP-seq. Mol Cell 40, 939-953

Zhao, J., Sun, B. K., Erwin, J. A., Song, J. J., and Lee, J. T. (2008). Polycomb proteins targeted by a short repeat RNA to the mouse X chromosome. Science 322, 750-756.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that disrupts binding of a Yin-Yang 1 (YY1)-binding long non-coding RNA (lncRNA) to Yin-Yang 1 (YY1) protein, the method comprising:
    (a) identifying an lncRNA that binds YY1 protein;
    (b) providing a cell-free sample comprising a YY1-binding lncRNA and YY1 protein, wherein the YY1-binding lncRNA binds to the YY1 protein thereby forming lncRNA-YY1 protein complexes;
    (c) contacting the cell-free sample with a test compound, wherein the test compound is a nucleic acid targeting the YY1-binding lncRNA;
    (d) isolating the lncRNA-YY1 protein complexes from the cell-free sample by contacting the cell-free sample comprising the lncRNA-YY1 protein complexes with an anti-YY1 antibody, wherein the anti-YY1 antibody specifically binds to YY1 protein, and immunoprecipitating the lncRNA-YY1 protein complexes; and
    (e) detecting formation of the lncRNA-YY1 protein complexes in presence and absence of the test compound, wherein a decrease in formation of lncRNA-YY1 protein complexes in the presence of the test compound as compared to formation of lncRNA-YY1 protein complexes in the absence of test compound indicates that the test compound disrupts the binding of the YY1-binding lncRNA to the YY1 protein.

2. The method of claim 1, wherein the YY1 protein is labeled.

3. The method of claim 1, further comprising wherein the YY1 protein not bound to YY1-binding lncRNA is isolated from the cell-free sample.

4. The method of claim 1, wherein the YY1-binding lncRNA is labeled.

5. The method of claim 1, wherein both the YY1 protein and the YY1-binding lncRNA are labeled.

* * * * *